United States Patent
Fitterer et al.

(10) Patent No.: US 12,268,363 B2
(45) Date of Patent: Apr. 8, 2025

(54) STEERABLE APPARATUS HAVING A SLIDEABLE IMAGING PROBE AND ASSOCIATED METHODS OF USE

(71) Applicant: INTUITIVE SURGICAL OPERATIONS, INC., Sunnyvale, CA (US)

(72) Inventors: Mimi Trinh Fitterer, Belmont, CA (US); Serena H. Wong, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 192 days.

(21) Appl. No.: 17/235,852

(22) Filed: Apr. 20, 2021

(65) Prior Publication Data
US 2021/0338064 A1    Nov. 4, 2021

Related U.S. Application Data

(60) Provisional application No. 63/019,167, filed on May 1, 2020.

(51) Int. Cl.
  *A61B 1/00* (2006.01)
  *A61B 1/018* (2006.01)
  *A61B 1/05* (2006.01)
(52) U.S. Cl.
  CPC .......... *A61B 1/018* (2013.01); *A61B 1/00087* (2013.01); *A61B 1/05* (2013.01); *A61B 2217/005* (2013.01); *A61B 2217/007* (2013.01)
(58) Field of Classification Search
  CPC ....... A61B 1/018; A61B 1/00087; A61B 1/05; A61B 2217/005; A61B 2217/007;
  (Continued)

(56) References Cited

U.S. PATENT DOCUMENTS

| | | | | |
|---|---|---|---|---|
| 5,166,787 A | * | 11/1992 | Irion | A61B 1/00181 348/75 |
| 2005/0165288 A1 | * | 7/2005 | Rioux | A61B 5/0084 600/7 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Timothy J Neal
(74) *Attorney, Agent, or Firm* — Haynes & Boone, LLP.

(57) ABSTRACT

An apparatus of the present technology generally includes an elongated shaft having a proximal portion and a distal portion, a first elongated channel extending from the proximal portion to the distal portion, a second channel extending from the proximal portion to the distal portion, and a slidable imaging probe disposed within the first elongated channel. The apparatus can be manually, robotically, and/or teleoperably steerable and is configured for delivery to a subject and/or positioning within a subject near or at a target location. Once the steerable apparatus has been successfully positioned at the target location, the imaging probe can be repositioned relative to the first elongated channel, thereby opening a working lumen. The working lumen and second channel are configured for removal of material from the target location within the subject by applying simultaneous activities including suction, irrigation, and/or deliver a tool to the target location.

17 Claims, 17 Drawing Sheets

(58) Field of Classification Search
CPC .............. A61B 17/0218; A61B 17/22; A61B 2017/003; A61B 2017/0034; A61B 2017/00349; A61B 2034/2051; A61B 2034/2059; A61B 2034/2061; A61B 2090/064; A61B 1/015; A61B 1/053; A61B 1/0125; A61B 1/00096

See application file for complete search history.

(56) References Cited

U.S. PATENT DOCUMENTS

| | | | | |
|---|---|---|---|---|
| 2007/0088247 | A1* | 4/2007 | Bliweis | A61B 17/3421 606/21 |
| 2010/0010294 | A1* | 1/2010 | Conlon | A61B 1/042 606/1 |
| 2013/0131445 | A1* | 5/2013 | Zerfas | A61B 17/22 600/104 |
| 2015/0119795 | A1* | 4/2015 | Germain | A61B 17/32002 604/28 |
| 2015/0133950 | A1* | 5/2015 | Shelton | A61B 17/2202 606/128 |
| 2016/0058502 | A1* | 3/2016 | Clark | A61B 18/1492 606/41 |
| 2016/0166320 | A1* | 6/2016 | Ciulla | A61B 18/26 606/14 |
| 2016/0174814 | A1* | 6/2016 | Igov | A61B 1/00101 600/106 |
| 2016/0235478 | A1* | 8/2016 | Bonneau | A61B 1/05 |
| 2017/0215964 | A1* | 8/2017 | Harrah | A61B 1/018 |
| 2017/0215965 | A1* | 8/2017 | Harrah | A61B 1/00137 |
| 2018/0085519 | A1* | 3/2018 | McCaffrey | A61B 5/0215 |
| 2018/0289394 | A1* | 10/2018 | Shah | A61B 17/320016 |
| 2019/0175799 | A1* | 6/2019 | Hsu | A61B 10/0283 |
| 2021/0093290 | A1* | 4/2021 | Finger | A61B 8/445 |
| 2021/0128189 | A1* | 5/2021 | Aljuri | A61B 18/04 |
| 2021/0219994 | A1* | 7/2021 | Muller | A61B 1/00066 |
| 2022/0202471 | A1* | 6/2022 | Schepis | A61B 18/1206 |

\* cited by examiner

STEERABLE APPARATUS HAVING A SLIDEABLE IMAGING PROBE AND ASSOCIATED METHODS OF USE

CROSS-REFERENCE TO RELATED PATENT APPLICATION(S)

This application claims the benefit of U.S. Provisional Patent Application No. 63/019,167, filed May 1, 2020, which is incorporated by reference herein in its entirety.

TECHNICAL FIELD

The present disclosure is generally directed to a steerable apparatus having an elongated channel configured to carry a slidable imaging probe that, when removed, provides a large working channel for applying suction or irrigation to a target location.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Minimally invasive medical tools may also include ablation instruments. Ablation instruments transmit energy in the form of electromagnetic waves to a targeted area of tissue, such as a tumor or other growth, within the patient anatomy to destroy the targeted tissue. Some minimally invasive medical tools and ablation instruments may be teleoperated or otherwise computer-assisted or delivered by a teleoperated, robotic, or otherwise computer-assisted system. Various features may improve the effectiveness of minimally invasive ablation instruments. Improved medical tools which provide imaging assisted navigation and function to perform a medical procedure at the region of interest within the patient's anatomy are needed.

SUMMARY

Disclosed herein are apparatuses, devices, systems, and methods for imaging and/or manipulating at least a portion of a patient's anatomy with a system for removal of material from a target location having an elongated shaft, an imaging probe, and a fluid circulation apparatus. The elongated shaft has a proximal portion, a distal portion, a first elongated channel extending from the proximal portion to the distal portion, and a second elongated channel extending from the proximal portion to the distal portion. The imaging probe is slidably disposed within a length of the first elongated channel and includes a distal head assembly and a proximal cable assembly. When at least the distal head assembly is removed, the first elongated channel is transformed to a delivery state. The fluid circulation apparatus is coupled to the second elongated channel so as to provide suction to the target location for removal of the material through the second elongated channel.

In some embodiments, a proximal cable assembly has a first diameter, the distal head assembly has a second diameter, and the first diameter is less than the second diameter. The distal portion of the elongated shaft can have a first diameter and the proximal portion can have a second diameter less than the first diameter. The imaging probe can be configured to be slidably disposed in a distal direction to remove the distal head assembly to transform the first elongated channel to the delivery state which provides for delivery of one or more removable tools and/or for delivery of fluid. The one or more removable tools is a basket, a laser, an ultrasound probe, a hydraulic fragmentation probe, a mechanical fragmentation probe, forceps, or a needle. In certain embodiments, at least one of the first elongated channel or the second elongated channel is slidably connected to the elongated shaft and configured to be distally advanced or proximally retracted independent of and relative to the elongated shaft.

In some embodiments, the fluid circulation apparatus is further coupled to the first elongated channel to provide irrigation when the first elongated channel is in the delivery state. The fluid circulation apparatus is configured to reverse flow through the first and second elongated channels by removing irrigation from the first elongated channel, removing suction from the second elongated channel, providing suction to the first elongated channel, and providing irrigation to the second elongated channel. The fluid circulation apparatus is further configured to measure pressure within first elongated channel. In certain embodiments, the first elongated channel or the second rigidizable channels are each rigidizable using fluid flow from the fluid circulation apparatus. In further embodiments, the imaging probe assembly further includes a body wherein the body is rigidizable.

In these and other embodiments, the elongated shaft comprises at least one of a shape sensor, a pressure sensor, or a force sensor. In certain embodiments, the shape sensor can be positioned along at least a portion of the length of the elongated shaft and the shape sensor can be comprised of at least one of a fiber shape sensor or a plurality of electromagnetic sensors.

In some embodiments, the first elongated channel, the second channel, or a combination thereof, is rigidizable. In certain embodiments, the system further comprising an elongated rigidizable spine slidably disposed within the elongated shaft from the proximal portion to the distal portion of the elongated shaft.

In these and further embodiments, the elongated shaft comprises a sidewall having a third elongated channel extending within the sidewall, an aperture positioned along the distal portion of the elongated shaft, and a standoff element disposed within the third elongated channel. The aperture can be in fluid communication with the third elongated channel. The standoff element can be deployable from the aperture and, in some embodiments, is a nitinol wire or a prong having an atraumatic tip.

In these and still further embodiments, the system further comprises a steerable sheath having a lumen and the elongated shaft is received within the lumen for delivery to the target location. The steerable sheath can further comprise at least one sensor, such as a shape sensor, a pressure sensor, or a force sensor In these and yet other embodiments, a method for retrieval of material from a target location using an extraction system can include (i) providing information at least during delivery of the extraction system to the target location, the extraction system comprising (a) an elongated shaft having a first lumen and a second lumen, (b) a slidable imaging probe disposed within the first lumen, wherein information includes imaging information and the slidable imaging probe captures the imaging information, (c) a fluid circulation system fluidly coupled to at least the second lumen; (ii) providing a delivery channel via the first lumen after the imaging probe has been at least partially removed from the first lumen; and (iii) providing suction, using the fluid circulation system, for retrieval of the material via the second lumen. The method further comprises (1) providing imaging information during retrieval of the material; (2) providing at least one removable tool to the target location through the delivery channel; (3) providing irrigation through the delivery channel, wherein the fluid circulation system is fluidly coupled to the first lumen; (4) providing the imaging information, to position the elongated shaft towards the material, (5) providing the imaging information for determining if the material is below a threshold size; (6) providing imaging information for determining whether the material has been retrieved from the target location; (7) providing imaging information for determining whether the material moved to an alternative location; (8) providing information for determining whether the elongated shaft is positioned proximate a tissue wall; (9) providing at least one deployable nitinol wire or at least one deployable prong having an atraumatic tip; and/or (10) providing an access sheath configured to carry the steerable apparatus. In some embodiments, providing the delivery channel includes inserting the imaging probe so the distal camera head is inserted beyond a distal end of the elongated shaft and removed from the first lumen. In some embodiments, the imaging information includes information about the location and/or the size of the material at the target location, and/or an image of the target location, such as a first image of the target location and a second image of at least one alternative location captured by repositioning of the slidable imaging probe or the elongated shaft.

In these and yet further embodiments, a system for delivery of an elongate shaft along a path to a target can include the elongated shaft comprising a proximal end, a distal end, and a first lumen extending therebetween; a rigidizable element received within the first lumen; and a processor communicatively coupled to the elongated shaft and the rigidizable element, the processor can be configured to (a) receive information during advancement of the elongated shaft towards the target, wherein the information includes imaging information, (b) detect a departure from a bend along the path based on the received information, (c) determine an incremental distance to advance the rigidizable element beyond the distal end of the elongated shaft, (d) relax the rigidizable element during advancing of the rigidizable element, (e) rigidize the rigidizable element after the rigidizable element has been advanced the incremental distance, (f) detect completion of navigation around the bend after advancing the elongated shaft over the rigidizable element, and/or (g) determine a radius of the bend based on the imaging information. In some embodiments, the imaging information comprises external imaging information including at least one of fluoroscopic images, computed tomographic information, magnetic resonance imaging images, or ultrasound images. In some embodiments, the imaging information further comprises endoscopic images, ultrasound images, or optical coherence tomographic images captured by the slidable imaging probe.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

Many aspects of the present technology can be better understood with reference to the detailed description along with the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

In the specification, it should be appreciated that like reference numerals are used to identify like elements illustrated in one or more of the figures for purposes of illustrating embodiments of the present disclosure and not for purposes of limiting the same.

DETAILED DESCRIPTION

Figure 1A:
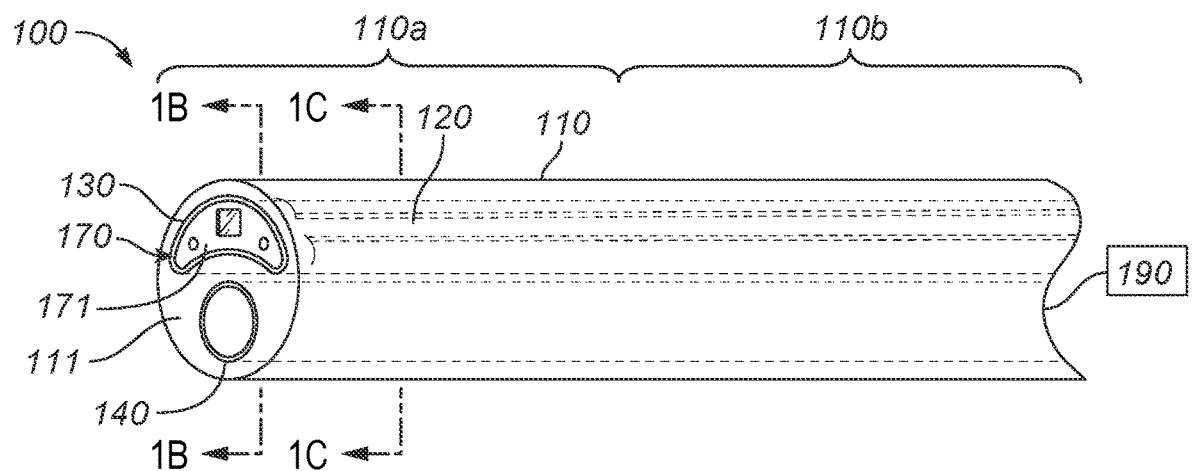
FIG. 1A illustrates a portion of an apparatus, such as a medical instrument, configured in accordance with various embodiments of the present technology.

Ureteroscopes are imaging-enabled apparatuses that are navigated through a delivery path, such as a patient's urethra, bladder, ureter, and kidneys, to examine the inside of a urinary tract or locate material, such as a kidney stone. Conventional ureteroscopes can be delivered under fluoroscopy aided with direct visualization from a fixed/non-removable real-time imaging probe, such as an endoscopic camera, integrated within the ureteroscope. The endoscopic visualization is essential to navigating to the target as well as to locating kidney stones within the kidney. Once material has been visualized and the ureteroscope has been delivered to a target location, material fragmentation and/or removal tools, such as lasers, baskets, meshes, and/or suction devices, are delivered through a working channel of the ureteroscope to retrieve the material. Accordingly, conventional ureteroscopes include continuous imaging (vision and lighting) and a working channel within the same device which makes it difficult to maintain a small diameter which can be desirable to minimize trauma to ureters and other structures.

Since the size and number of channels within a ureteroscope is restricted by the dimension of the ureteroscope being configured for delivery within narrow delivery paths to avoid causing damage to anatomical structures, conventional ureteroscopes are not designed for simultaneous fragmentation of larger material (e.g., stones) and removal of the fragmented material. They are rather designed for the laser to be exchanged with a basket or suction device which add unnecessary steps to the procedure, thereby increasing duration of the procedure, risk for error when removing material, and risk that some material may move during fragmentation and therefore not be removed.

In addition, conventional ureteroscopes are either manually steerable or delivered over a guide wire. Neither delivery approach allows for the ureteroscope to be maintained in a stable position. Thus, once material is located and the ureteroscope is positioned towards the material, the ureteroscope can shift while tools such as baskets, meshes, lasers, or suction devices are exchanged through the working channel.

The present disclosure is directed to apparatuses configured for, or otherwise adapted to, use in a procedure that requires fragmenting, suction, irrigation, and/or endoscopic visualization such as ureteroscopes for removing material at an anatomic location. Apparatuses configured for, or otherwise adapted to, such uses include two channels, the first acts as an open working channel while the second carries a slidable imaging probe that, when re-positioned, provides an additional channel. Each channel allows for delivery of tools or irrigation/suction to be applied to a target location. The present disclosure therefore addresses an unmet need of providing apparatuses and associated methods that include fragmenting and suction within the same apparatus, while maintaining a thin, small diameter profile. Some embodiments can additionally provide for constant real time visualization and a stable delivery platform that allow for the ureteroscope to maintain a position at the target location while tools are being exchanged.

Thus, the present disclosure is generally directed to an apparatus, such as a medical instrument (e.g., a ureteroscope), having an elongated channel configured to carry a slidably removable imaging probe, and associated methods. Positioning of the apparatus within a subject can be performed in any combination of manually, robotically, or teleoperably with the slidable imaging probe disposed within the apparatus. The apparatus may be steerable or may include a steerable sheath providing a delivery lumen for the apparatus. The steerable sheath may comprise at least one sensor, wherein the at least one sensor is a shape sensor, a pressure sensor, or a force sensor. Once the apparatus has been successfully positioned at a target location, the imaging probe can be re-positioned, thereby creating a more open lumen useful for applying suction and/or irrigation and/or delivering a tool for fragmenting or removing material from the target location within the subject. The apparatus also includes an additional channel configured as a working channel, thereby allowing for two interventions to be performed at the target location at the same time through the open lumen and the working channel (e.g., irrigation and suction or tool use (fragmenting) and suction).

In some embodiments the imaging probe can be redelivered via the working lumen after the apparatus has been positioned if the material moves from the target location and imaging is needed to determine a new target location and/or re-position the apparatus. In other embodiments, once the apparatus has been delivered to the target location, the imaging probe may be inserted, opening the lumen but also providing continuous visualization to track material as it moves to aid in re-positioning of the apparatus.

Apparatuses configured in accordance with the present technology can also include one or more standoff elements configured to be deployed to maintain an acceptable distance from anatomical tissue, such as an inner wall of an organ, e.g. the kidney. In some embodiments, at least a portion of the apparatus can be re-positioned while the standoff elements are deployed. In further embodiments, the standoff instruments can be retracted and the device re-positioned. Once the apparatus has been re-positioned, the standoff elements can be re-deployed to maintain another pose.

In some embodiments, during delivery of the apparatus to the target location, portions of the apparatus may be configured to be selectively rigidized, which is expected to be useful during delivery, to the target location, and is further useful to avoid contacting one or more anatomical structures in the subject.

Specific details of several embodiments of the present technology are described herein with reference to FIGS. 1A-18B. Although many of the embodiments are described below in the context of navigating and performing medical procedures within a patient's urinary tract, other applications and other embodiments in addition to those described herein are within the scope of the present technology. For example, unless otherwise specified or made clear from context, the apparatuses, systems, and methods of the present technology can be used for various image-guided medical procedures, such as medical procedures performed on, in, or adjacent hollow patient anatomy, and, more specifically, in procedures for surveying, biopsying, ablating, or otherwise treating tissue within and/or proximal the hollow patient anatomy. Thus, for example, the apparatuses, systems, and methods of the present disclosure can be used in one or more medical procedures associated with other patient anatomy, such as the vasculature, kidneys, bladder, lungs, and/or heart of a patient. In addition, the present disclosure generally refers to ureteroscopes, however the present disclosure also applies to any apparatus useful for a procedure that requires suction and/or irrigation and delivery of tools as well as partial or continuous endoscopic visualization.

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology. In some instances, well-known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

As used herein, the term "operator" shall be understood to include any type of personnel who may be performing or assisting a medical procedure and, thus, is inclusive of a physician, a surgeon, a doctor, a nurse, a medical technician, other personnel or user of the technology disclosed herein, and any combination thereof. As used herein, the term "patient" should be considered to include human and/or non-human (e.g., animal) patients upon which a medical procedure is being performed.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1B:
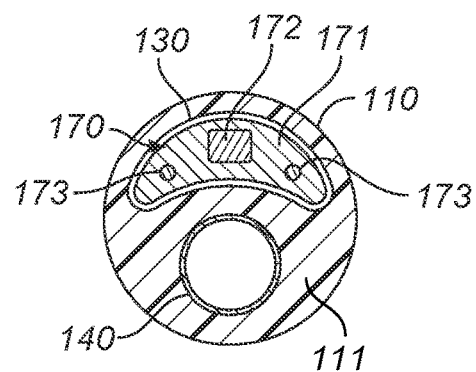
FIG. 1B is a cross-sectional view taken along line 1B-1B of FIG. 1A.

FIG. 1A illustrates a portion of a steerable apparatus 100 (which may be a therapeutic, diagnostic, or imaging medical instrument, such as a ureteroscope) configured in accordance with various embodiments of the present technology. FIG. 1B is a cross-sectional view taken along line 1B-1B of FIG. 1A. Referring to FIGS. 1A and 1B together and as will be discussed below, a slidable imaging probe 170 is slidably carried by an elongated flexible shaft 110 ("elongated shaft 110") within a length of a first channel 130. The apparatus 100 of the present technology is configured to be delivered to a subject through an anatomical opening, such as a natural orifice, or an opening generated in the subject by an operator, such as through an incision. and parked at a pose near a target location in the subject. The apparatus 100 may be manually steerable for delivery, positioning and re-positioning within the subject, and during removal from the subject using pull wires coupled to a distal end of the apparatus and controlling bending of the apparatus by applying tension via a manual handle to the pull wires at a proximal end of the apparatus. In other embodiments, however, the apparatus 100 may be robotically steerable (using motorized actuation for tensioning of the pull wires) and/or teleoperated or may be manually steerable but delivered using robotically steerable or teleoperated systems. These and additional methods of use are described below in further detail below with reference to FIGS. 10A-18B.

As shown in FIG. 1A, the elongated shaft 110 of the apparatus 100 has a distal end portion 110a, a proximal end portion 110b, and a distal face 111. The distal end portion 110a has a first diameter that is substantially similar to, or in some embodiments the same as, a first diameter of the proximal end portion 110b. In other embodiments, the first diameter of the distal end portion 110a can be different from (e.g., can be less than) the first diameter of the proximal end portion 110b. In some embodiments, the elongated shaft 110 is formed of a uniform material (e.g., a polymer or a thermoplastic polyurethane, such as Pellethane or Tecothane). In other embodiments, the elongated shaft 110 is formed of a plurality of materials. For example, a material composition of the elongated shaft 110 can vary along its length (e.g., over the proximal end portion 110b and/or over the distal end portion 110a). As a specific example, a first section of the proximal end portion 110b of the elongated shaft 110 can be formed of Tecothane 69D EG, a second section of the proximal end portion 110b distal the first section can be formed of Pellethane 55D, and a third section of the proximal end portion 110b distal the second section can be formed of Pellethane 80A EG. Additionally, or alternatively, a first section of the distal end portion 110a of the elongated shaft 110 can be formed of Tecothane 69D, a second section of the distal end portion 110a distal the first section can be formed of Pellethane 55D, and a third section of the distal end portion 110a distal the second section can be formed of Pellethane 80A. The dimensions (e.g., the lengths, the thicknesses, etc.) and/or durometers of the various sections can be uniform or can vary.

Varying the material composition, dimensions, and/or durometers of the elongated shaft 110 along its length is expected to vary a stiffness of the elongated shaft 110 along its length. For example, one or more flexible materials that are relatively more resistant to bending (e.g., that are relatively stiffer) can be used along the proximal end portion 110b of the elongated shaft 110 to provide the elongated shaft 110 a desired support or rigidity along the proximal end portion 110b. Continuing with this example, flexible materials that are relatively less resistant to bending (e.g., that are relatively less stiff) can be used along the distal end portion 110a of the elongated shaft to provide the elongated shaft 110 a desired rigidity along the distal end portion 110a. The desired rigidity or stiffness along the distal end portion 110a in this example can be less than the desired rigidity or stiffness along the proximal end portion 110b such that the distal end portion 110a of the elongated shaft 110 is more flexible than the proximal end portion 110b and/or such that distal sections of the distal end portion 110a are more flexible than proximal sections of the distal end portion 110a. This is expected to (i) facilitate a greater amount of control over finer motions of the distal end portion 110a of the shaft 110 and/or (ii) facilitate easier navigation of the distal end portion 110a of the elongated shaft 110 through tortuous patient anatomy.

Additionally, or alternatively, the elongated shaft 110 can include cut outs or notches (not shown) to achieve a desired stiffness or rigidity of the elongated shaft 110. For example, the elongated shaft 110 can include cut outs along the distal end portion 110a and/or along the proximal end portion 110b. The dimensions and/or spacing of the cut outs can be uniform or can vary. For example, dimensions of the cut outs can increase along the length of the elongated shaft 110 such that distal sections of the elongated shaft 110 are more flexible (e.g., are less stiff) than proximal sections of the elongated shaft 110. In these and other embodiments, spacings between adjacent cut outs in the elongated shaft 110 can decrease along the length of the elongated shaft 110 to achieve a similar result (e.g., distal sections of the elongated shaft 110 that are more flexible than proximal sections). A stiffness or rigidity of any one or more of elongated shafts 310, 510, 610, 710, 1010, 1110, 1510 discussed in detail below with respect to FIGS. 3A, 5, 6A, 7A, 10A, 11A, and 15A, respectively, can be uniform or can vary in a manner consistent with the discussion of the elongated shaft 110 of FIG. 1A above (e.g., by varying material compositions, material durometers, shaft or material dimensions, cut out dimensions, cut out spacings, etc.).

Referring to FIGS. 1A and 1B together, the elongated shaft 110 further comprises a sidewall 120 (FIG. 1A) that defines the first channel 130 and a second channel 140 (e.g., a working channel). The first channel 130 and the second channel 140 both extend longitudinally from at least the proximal end portion 110b (FIG. 1A) through the distal end portion 110a (FIG. 1A) of the elongated shaft 110. In the illustrated example, the first channel 130 and second channel 140 are positioned to run side-by-side in a non-concentric configuration.

The slidable imaging probe 170 is configured to be slidably received by, carried by, positioned within, and slidably removed from the first channel 130 when the apparatus 100 is located at a pose. The slidable imaging probe 170 can include a camera head 171 and a proximal cable assembly 175 (illustrated in FIG. 1C). The camera head 171 can include a camera 172 (FIG. 1B) and a set of light fibers 173 (FIG. 1B) for illuminating a target site. In the embodiment illustrated in FIGS. 1A-1C, the camera head 171 is shown as an arc-shaped head and the first channel 130 is shown as an arc-shaped lumen, providing for a round cross-sectional working channel 140. During delivery of the apparatus 100 to an anatomical site (e.g. bladder, ureter, kidneys) and positioning of the apparatus 100 towards a target (e.g. kidney stone), the imaging probe 170 can be positioned within the first channel 130 for direct visualization. Once the target has been located and the apparatus 100 has been properly positioned, the slidable imaging probe 170 can be retracted and removed from a proximal end of the apparatus 100, transforming the first channel 130 is into an open lumen useful for applying suction, irrigation, and/or delivering a tool to a target location in a subject. Thus, once at the target location, the apparatus 100 provides two open channels 130 and 140 such that each channel can be used for different functions.

Figure 1C:
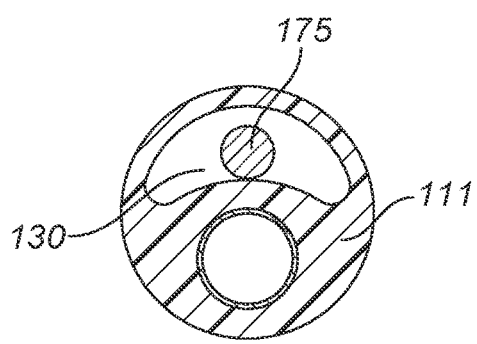
FIG. 1C is a cross-sectional view taken along line 1C-1C of FIG. 1A.
Figure 2A:
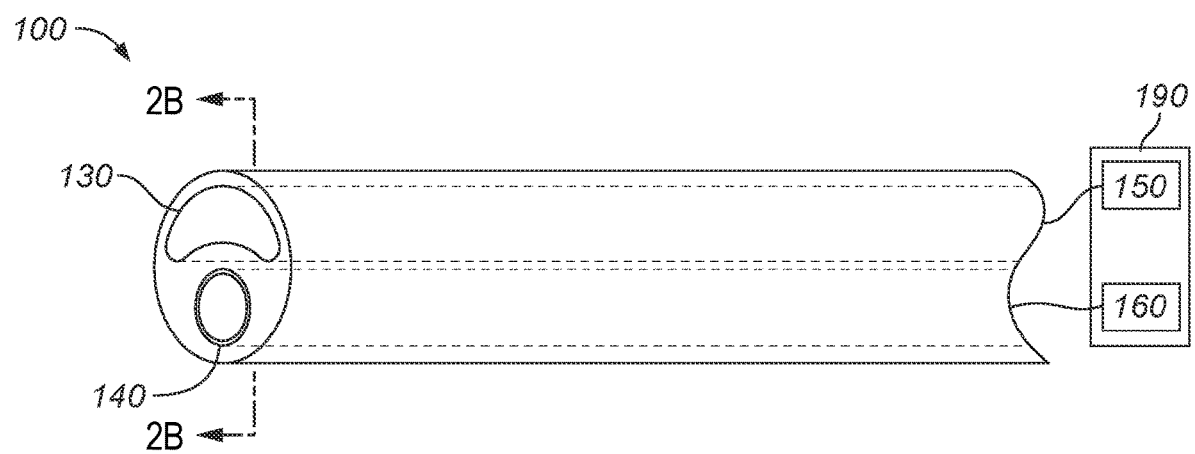
FIG. 2A illustrates a portion of an apparatus, such as a medical instrument, configured in accordance with embodiments of the present technology.
Figure 2B:
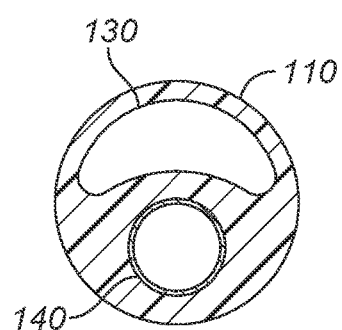
FIG. 2B is a cross-sectional view taken along line 2B-2B of FIG. 2A.
Figure 5:
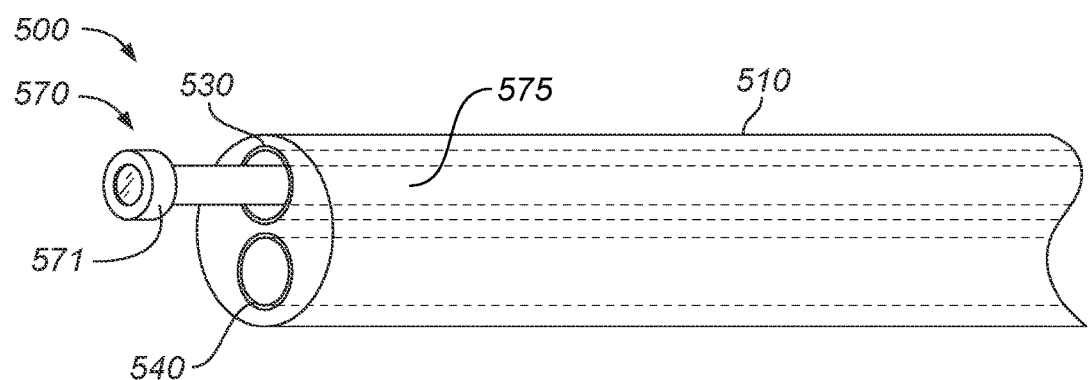
FIG. 5 illustrates a portion of an apparatus, such as a medical instrument, configured in accordance with embodiments of the present technology.

As described in greater detail below, the first channel 130 and/or the second channel 140 are sized and shaped such that tools/surgical instruments may be slidably advanced/retracted therethrough. In some embodiments, the second channel 140 has a diameter greater than a diameter of the first channel 130. In other embodiments, however, the first and/or second channels 130 and 140 may have different diameters/configurations. Further, although the apparatus 100 is illustrated with two channels 130 and 140, apparatuses configured in accordance with other embodiments of the present technology can include a different number, shape, and/or position of channels. For example, an apparatus of the present technology can include one, or three or more channels in some embodiments. Additionally, while the first channel 130 is illustrated as an arc and the second channel 140 is illustrated as circular, all or a subset of the channels can have an arced, circular, non-circular (e.g., "D"-shaped, square, rectangular, polygon, or otherwise rectilinear, etc.) cross-sectional shape. Furthermore, the first channel 130 and the second channel 140 (or associated lumens, such as a first lumen or a second lumen, respectively) can be concentric or non-concentric. Accordingly, an imaging probe may be provided with a camera head shaped with a circular or non-circular profile, and the camera head can be shaped to be received within a corresponding channel (e.g., a non-circular camera head may be inserted within a non-circular or circular shaped channel or a circular camera head may be in circular or non-circular lumen). For example, as illustrated in FIG. 5, an apparatus 500 having an elongated shaft 510 is shown. The elongated shaft includes a first circular channel 530 and a second channel 540. An imaging probe 570 having a circular camera head 571 is inserted into the circular channel 530 of the elongated shaft 510. In one embodiment, for smaller stones, the apparatus 100 is configured to provide simultaneous suction and irrigation to the target location within the subject. The first channel 130 and the second channel 140 may be fluidly coupled to a fluid circulation apparatus 190 (e.g., vacuum apparatus, a pressure apparatus, or a combination thereof). For example, the fluid circulation apparatus can be configured to measure pressure within first elongated channel. One channel may provide suction to remove the stones from the anatomical target location while the other channel may provide irrigation to generate a constant airflow and/or fluid flow. In one example, as illustrated in FIGS. 2A and 2B, the first channel 130 (once the imaging probe 170 (FIGS. 1A-1C) is removed) may be fluidly coupled to an irrigation apparatus 150 and the second channel 140 may be fluidly coupled to a suction apparatus 160 providing for a constant flow for removal of stone fragments through channel 140. As another example, the first channel 130 may be fluidly coupled to the suction apparatus 160 and the second channel 140 may be fluidly coupled to the irrigation apparatus 150. In some embodiments, the larger channel may be used for suction while the smaller channel may be used for irrigation, thereby allowing for a larger capacity for removal of stones. In some embodiments, hardware for both suction and irrigation are included within the fluid circulation apparatus 190 and the direction of airflow and/or fluid flow can be applied in a first direction and then reversed to a second direction that differs from and/or is opposite from the first direction.

In some embodiments, a pressure monitor may be coupled to first channel 130 and/or second channel 140 for sensing a position and/or a shape of the steerable apparatus during performance of a procedure. In some embodiments, the pressure monitor is configured to sense if the apparatus is misaligned or the pose has changed from a first pose to a second pose indicating, for example kinking along a length of the apparatus. For example, the apparatus may become misaligned or the pose may change when the operator O is irrigating and/or suctioning at the target location if the distal tip of the apparatus is too close to an anatomical structure. In another example, a change in pressure may indicate that a stone or stone fragment may be lodged within the first channel 130 or the second channel 140. Additionally, or alternatively, a shape sensing fiber, as will be described in detail below, may be integrated within first channel 130, second channel 140, or a separate channel (not shown) providing shape data along the length of the apparatus). Shape data can be used to determine unexpected changes in position and/or shape of the apparatus indicative of misalignment or lodging of stones or stone fragments.

In another embodiment, to treat larger stones which require breakage in order to be removed through the apparatus, a laser or other fragmentation device can be delivered through one channel and the other channel can provide simultaneous suction to remove stone dust or fragments as they are generated. This eliminates an extra workflow tool exchange necessary for single channel devices and reduces the risk of losing smaller stones within patient anatomy.

Figure 3A:
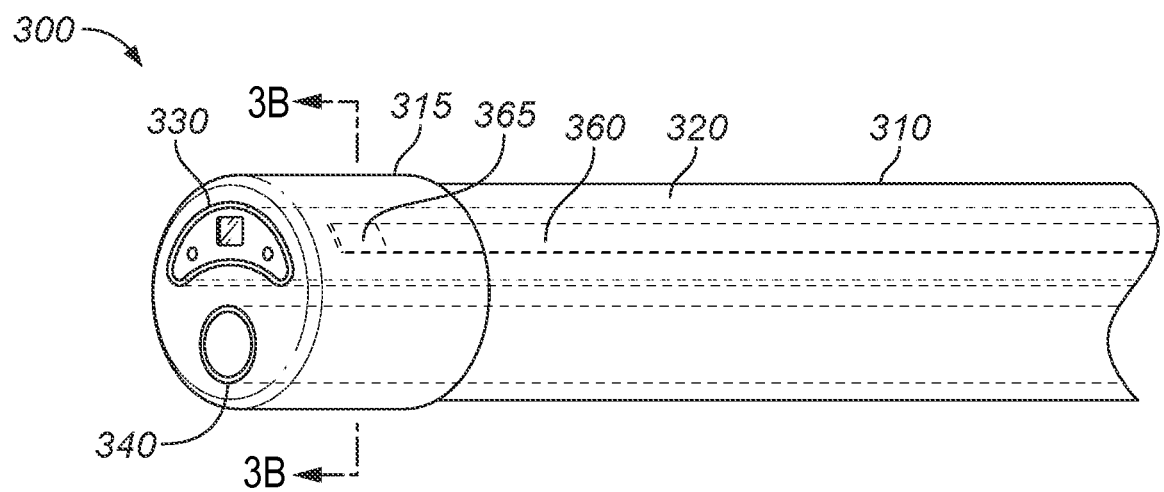
FIG. 3A illustrates a portion of an apparatus, such as a medical instrument, configured in accordance with embodiments of the present technology.
Figure 3B:
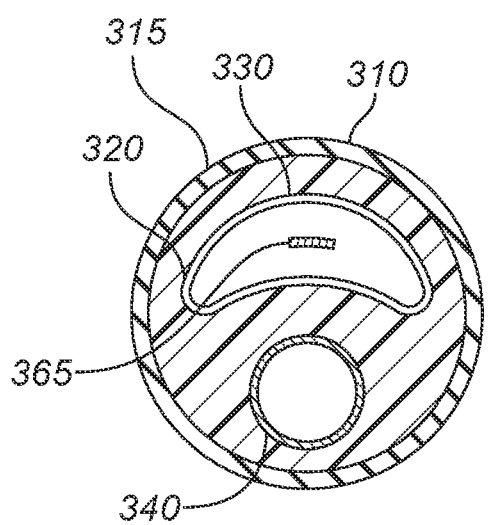
FIG. 3B is a cross-sectional view taken along line 3B-3B of FIG. 3A.

FIG. 3A illustrates an example for use in removal of larger stones including a portion of another steerable apparatus 300 configured in accordance with various embodiments of the present technology. FIG. 3B is a cross-sectional view taken along line 3B-3B of FIG. 3A. Unless noted otherwise and regardless if illustrated in FIG. 3A or FIG. 3B, the apparatus 300 includes elements, features, and configurations that are generally similar to those, or the same as those, of the apparatus 100 described herein. Referring to FIGS. 3A and 3B together, the apparatus 300 includes an elongated shaft 310 which includes a sidewall 320 that defines a first channel 330 and a second channel 340 extending longitudinally from a proximal end to a distal tip 315 of the elongated shaft 310. The apparatus 300 further comprises a distal tip 315 disposed at a distal end of the apparatus 300. The tip 315 may be composed of a material, such as stainless steel or other suitable material, for use with the energy emitting device 360 (FIG. 3A) as described in more detail below.

As previously described, a slidable imaging probe (such as the imaging probe 170 of FIG. 1A) may be received within the first channel 330 during delivery of the apparatus 300 to target anatomy and may be removed from the first channel 330 once the apparatus 300 is properly positioned (e.g., adjacent a target kidney stone). Subsequently with the first channel 330 open, the energy emitting device 360 (FIG. 3A), such as a laser, ultrasound, hydraulic, or mechanical device, configured for fragmenting target material of a patient (e.g., kidney stone(s), target tissue, etc.) is slidably positioned in the first channel 330. For purposes of illustration, the energy emitting device 360 in the embodiments shown in FIGS. 3A and 3B is a laser having an energy delivery tip 365. Similar to slidable imaging probe 170, the energy emitting device 360 may be advanced distally and/or retracted proximally within the first channel 330 relative to the elongated shaft 310. In other embodiments, however, while the energy emitting device 360 provides energy for fragmenting stones too large to be retrieved through the second channel 340, suction can be simultaneously provided to the second channel 340 to retrieve stone fragments and stone dust generated by the fragmentation process. Additionally, to increase fluid flow, irrigation may be provided by the first channel 330 through space around the energy emitting device 360.

In other embodiments, the energy emitting device 360 may be carried by the second channel 340 and/or the second channel can provide irrigation, and the first channel 330 can be simultaneously used to provide suction to retrieve stone fragments and stone dust. In yet another embodiment, the energy emitting device 360 may be included within another portion of the elongated shaft 310, such as integrally formed within the apparatus 300 itself. In a separate embodiment, a retrieval tool such as a basket or mesh may be provided to retrieve stone fragments. The retrieval tool may be provided within one channel while an energy emitting device may be provided in a separate channel. For example, the energy emitting device may be provided within the first channel 330 and the retrieval tool (not shown) may be provided within the second channel 340. Additionally, in order to retrieve smaller stones and stone dust, suction may be provided within the second channel 340 in the space around the retrieval tool and irrigation may be provided within the first channel 330 in the space around the energy emitting device 360. Alternatively, the energy emitting device and irrigation may be provided through the second channel 340 and the retrieval tool and suction may be provided through the first channel 330.

Figure 4:
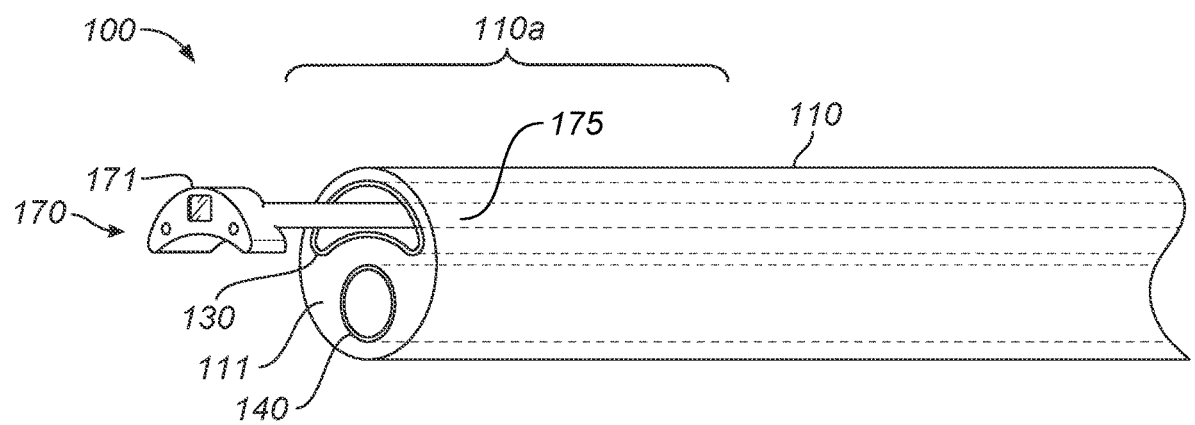
FIG. 4 illustrates a portion of an apparatus, such as a medical instrument, configured in accordance with various embodiments of the present technology.

Referring to FIGS. 1A-2B and 4 together, the slidable imaging probe 170 is configured to be extended distally from the distal end portion 110a of the elongated shaft 110. For example, FIG. 4 illustrates the apparatus 100 of FIGS. 1A-2B in an alternative configuration in accordance with embodiments of the present technology. As shown, the slidable imaging probe 170 is advanced distally from the distal end portion 110a of the elongated shaft 110, thereby exposing a portion of the slidable imaging probe 170. In some embodiments, the slidable imaging probe 170 is distally advanced toward a second target location spaced apart from the first or initial target location. Distally advancing the slidable imaging probe 170 during operation is expected to provide further visual feedback to the operator O regarding anatomical structures, material disposed between the first target location and the second target location, and/or the position of the apparatus 100. In further operation, the imaging probe 170 may be further advanced relative to the distal face 111 of the elongated shaft 110 and/or retracted proximally relative to the distal face 111 depending on needs for better visualization of the target location or stones.

As illustrated in FIG. 4, advancing the camera head 171 of the imaging probe 170, opens the first channel 130 leaving only the cable assembly 175. The additional room around the cable assembly 175 can be used for suction, irrigation, and/or tool delivery while still providing continuous vision during a stone removal process. As shown in FIG. 1B (a cross-sectional view taken along line 1B-1B of FIG. 1A), the camera head 171 of the slidable imaging probe 170 is disposed at or near a distal face 111 of the elongated shaft 110. The cross-sectional diameter of the camera head 171 generally corresponds to the diameter of the first channel 130 such that there is very little or no clearance around the head 171 (e.g., just sufficient enough clearance such that the head 171 can slidably move along the first channel 130). As best seen in FIG. 1C (a cross-sectional view taken along line 1C-1C of FIG. 1A), the cross-sectional diameter of the cable assembly 175 is less than the cross-sectional diameter of the camera head 171 (and the diameter of the first channel 130) such that there is gap/space between the cable assembly 175 and inner sidewalls of the first channel 130), which allows suction and/or irrigation or tool delivery to be provided by the first channel 130 but also still simultaneously providing continual visualization while the imaging probe 170 is slidably received within the first channel 130. Thus, in one example, the first channel 130 can provide irrigation while the second channel 140 provides suction establishing a constant flow for retrieval of small stones and dust. In another example, the first channel 130 can provide a working lumen for delivery of the fragmentation device (and irrigation in some embodiments) while the second channel 140 can simultaneously provide suction (and a retrieval device in some embodiments) to retrieve the fragmented stones and stone dust during the fragmentation process. In yet another example, the second channel 140 can provide a working lumen for delivery of the fragmentation device (and irrigation in some embodiments) while the first channel 130 can simultaneously provide suction (and a retrieval device in some embodiments) to retrieve the fragmented stones and stone dust during the fragmentation process. In all examples, because the imaging probe 170 has been distally advanced (instead of being removed) from the apparatus 100 and thus the camera head 171 is positioned within anatomy, real time images of the stones can be provided, thereby allowing for an operator O to visualize when a stone has been completely retrieved. Not only does this provide a measure of safety during fragmentation, in some examples, the operator O may determine that a stone has moved and may reposition the apparatus 100. In other embodiments, the operator O may begin stone retrieval using the first channel 130 for irrigation and the second channel 140 for suction, and visually identify that the stone may be too large. The operator O can then stop suction within the second channel 140, deliver an energy emitting device (such as energy emitting device 360—FIG. 3A), reverse flow within the first channel 130 by stopping irrigation and applying suction, then proceed with fragmenting and retrieving the stone.

Figure 6A:
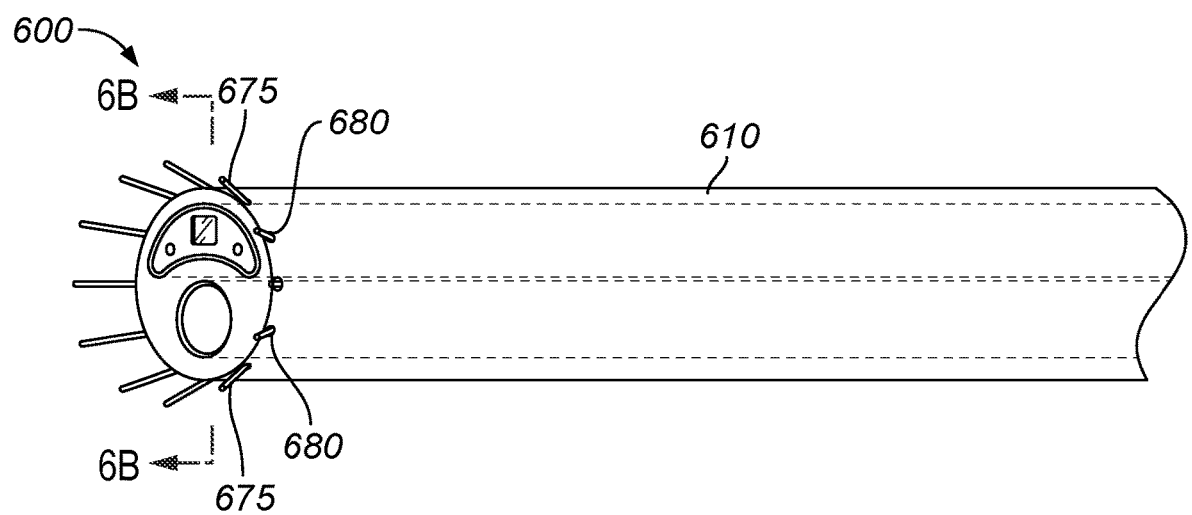
FIG. 6A illustrates a portion of an apparatus, such as a medical instrument, configured in accordance with embodiments of the present technology.
Figure 6B:
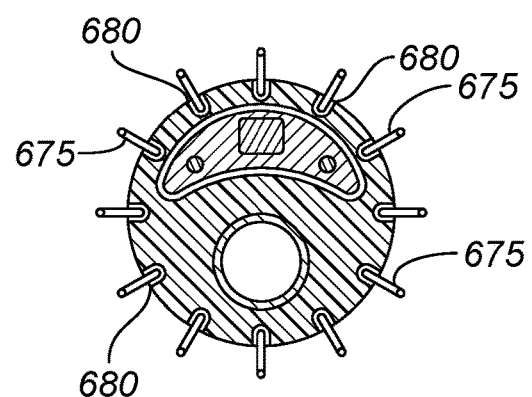
FIG. 6B is a cross-sectional view taken along line 6B-6B of FIG. 6A.
Figure 7A:
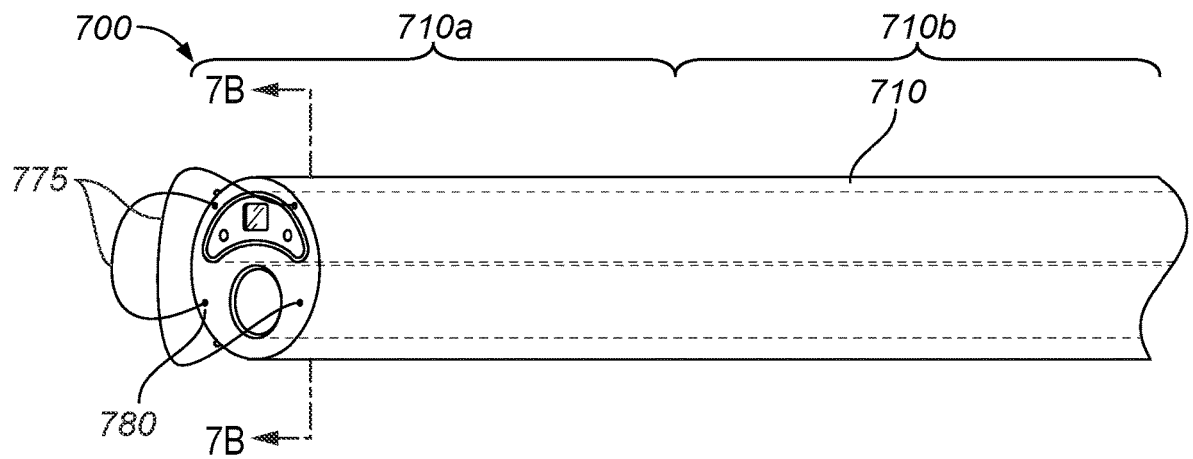
FIG. 7A illustrates a portion of an apparatus, such as a medical instrument, configured in accordance with additional embodiments of the present technology.
Figure 7B:
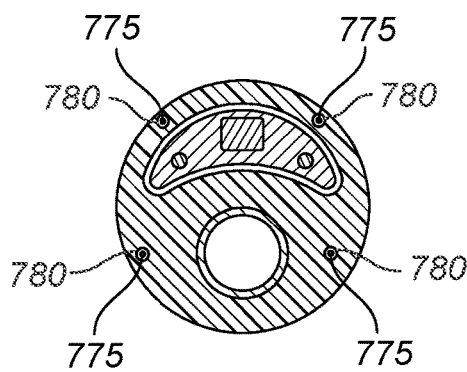
FIG. 7B is a cross-sectional view taken along line 7B-7B of FIG. 7A.

FIGS. 6A and 7A illustrate a portion of other steerable apparatuses 600 and 700 ("apparatus 600" and "apparatus 700") configured in accordance with various embodiments of the present technology. FIGS. 6B and 7B are cross-sectional views taken along line 6B-6B of FIGS. 6A and 7B-7B of FIG. 7A, respectively. Unless noted otherwise and regardless if illustrated in any of FIGS. 6A-7B, apparatuses 600 and 700 each include elements, features, and configurations that are generally similar to those, or the same as those, of the apparatuses 100, 300, and 500 described herein.

In some embodiments, a target stone may be positioned in close proximity to an organ wall so that as suction is applied to a working channel, tissue is accidentally caught within an opening or lumen of the working channel thereby clogging the lumen. In some examples, such as described above with respect to apparatus 100 of FIG. 4, constant vision is available so an operator O can visually identify if the instrument distal face is too close to an anatomical wall or if loose tissue is being pulled close to the distal end of the instrument. The operator O can then reposition apparatus 100 accordingly. But the apparatus may not be able to be repositioned without losing access to the target stone or an imaging probe is removed as illustrated in FIG. 2A, so the user would not be able to visually identify tissue. Thus, in another variation, the instrument can include a deployable standoff device to space a distal end of an apparatus from the tissue wall prior to applying suction.

Referring first to FIGS. 6A and 6B together, the apparatus 600 includes an elongated shaft 610 having a plurality of sidewall channels (not shown) extending longitudinally along the length of the elongated shaft 610. The sidewall channels each terminate in an aperture 680 disposed radially about the elongated shaft 610. Each sidewall channel carries a deployable (e.g., radially and/or axially) and extendable (e.g., radially and/or axially) standoff element 675 that may be deployed and extended through the respective apertures 680. During operation, the standoff elements 675 are configured to be deployed by the operator to assist in positioning/bracing the apparatus 600 at a desired target location within the subject and/or maintaining a desired pose of the apparatus 600. While not shown in FIGS. 6A and 6B, the standoff elements 675 can be disposed longitudinally along the elongated shaft 610 to improve flow along a length of an anatomical passage, such as a ureter. One or more pressure sensors can be configured to provide pressure information to the operator O which correlates to a dimension of the anatomical passage, such as a diameter of a ureter. The pressure sensors described herein and with respect to FIGS. 6A and 6B can also be incorporated into other embodiments of the present technology, such as apparatus 1500 illustrated in FIGS. 15A-15C.

Without intending to be limiting, the deployable and extendible standoff elements 680 may be a wire, a prong, a structure having a curvature such as an arc that extends along at least a portion of the subject's anatomical wall, and/or a cage (e.g., a mesh cage). The deployable and extendable standoff elements 680 may be formed from nitinol and (optionally) include an atraumatic tip. In still other embodiments, the standoff elements 680 may have other arrangements/configurations and/or be composed of other materials.

Referring next to FIGS. 7A and 7B together, the apparatus 700 includes an elongated shaft 710 having a distal end portion 710a, a proximal end portion 710b, and a plurality of longitudinal sidewall channels (not shown) that each terminate in an aperture 780 disposed radially about a distal end of the elongated shaft 710. Each sidewall channel carries an elongated standoff element 775 (e.g., wire or thread) that may be distally extended (e.g., radially and/or axially) and/or proximally retracted (e.g., radially and/or axially). During operation, the standoff elements 775 are configured to be deployed by the operator to assist in positioning/bracing the apparatus 700 at a desired target location within the subject and/or maintaining a desired pose of the apparatus 700. The standoff elements 775 are also configured to move at least a portion of material at the target location toward the distal end of the elongated shaft 710 when the operator is proximally retracting the standoff elements 775 to assist in suctioning the material.

Figure 8:
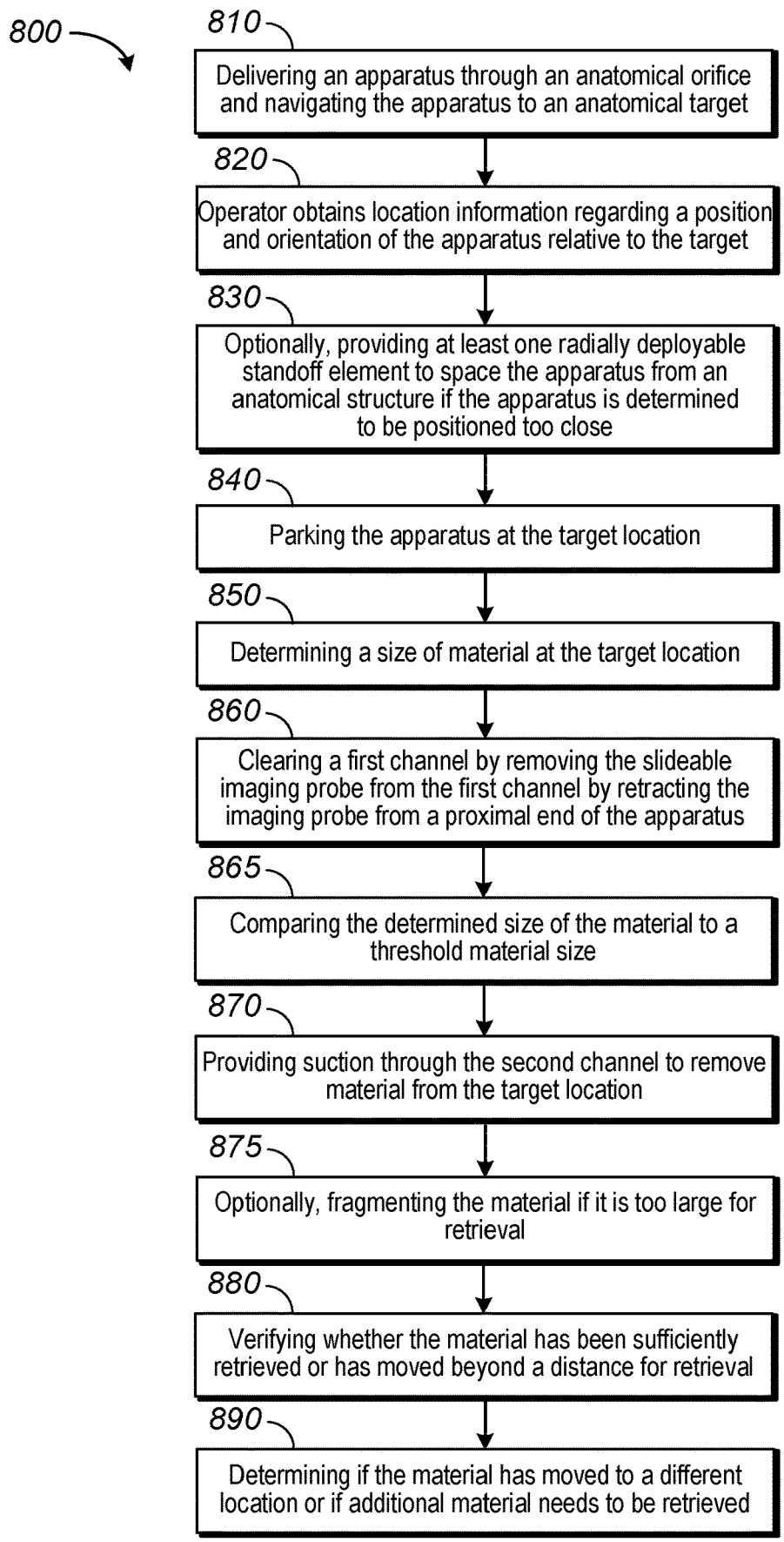
FIG. 8 is a simplified flow diagram of a method for delivering an apparatus having a removable imagining probe removed from the apparatus, such as a medical instrument, to a subject in need thereof in accordance with embodiments of the present technology.
Figure 9:
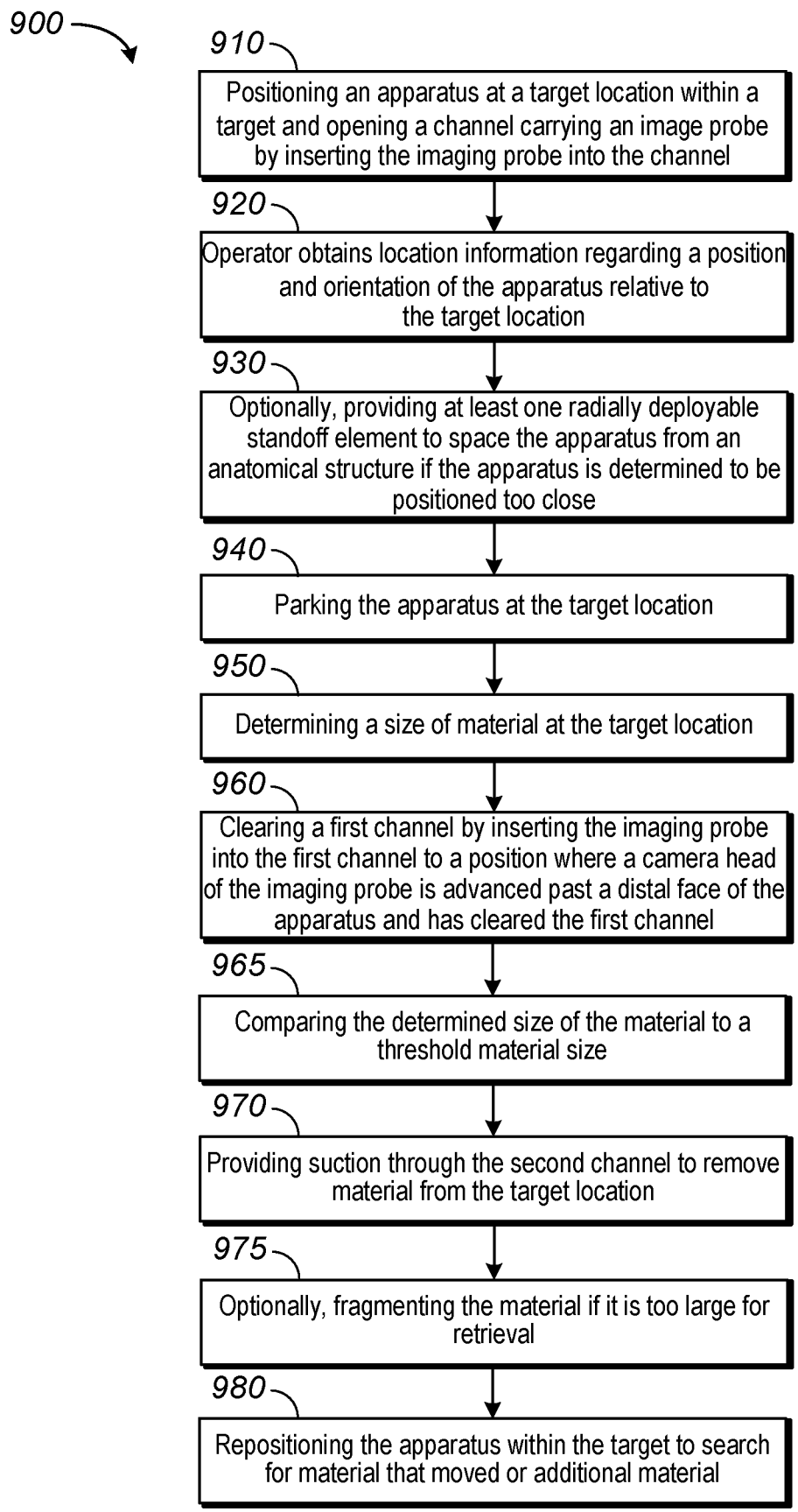
FIG. 9 is another simplified flow diagram of a method for delivering an apparatus having a removable imagining probe extended distally from the apparatus, such as a medical instrument, to a subject in need thereof in accordance with embodiments of the present technology.

FIGS. 8 and 9, illustrate examples of simplified flow diagrams of methods of positioning a steerable apparatus at a treatment location for retrieval of target material in a subject in accordance with various embodiments of the present technology. The methods are illustrated as a set of steps or processes and described at least in part below with further reference to FIGS. 16-17B. All or a subset of the steps of the methods can be executed by various instruments, apparatuses, devices, components thereof, components or devices of a robotic or teleoperated system, such as the system 1600 and the system 1700 illustrated in FIGS. 16 and 17A-17B or other suitable systems. Additionally, or alternatively, all or a subset of the steps of the methods can be executed by an operator (e.g., a physician, a user, etc.) of various instruments, apparatuses, devices, components thereof, components or devices of a robotic or teleoperated system, such as the system 1600 and the system 1700 illustrated in FIGS. 16 and 17A-17B or other suitable systems. Although the steps of the methods are discussed and illustrated in a particular order, the methods are not so limited. In other embodiments, one or more steps of the method can be performed in a different order. Moreover, a person of ordinary skill in the relevant art will recognize that methods can be altered and still remain within these and other embodiments of the present technology. For example, one or more steps of methods can be omitted and/or repeated in some embodiments. Furthermore, any one or more of the steps of the methods can be executed in accordance with the discussion above.

FIG. 8 illustrates a simplified flow diagram of a method 800 of positioning a steerable apparatus at a treatment location for retrieval of target material from a subject, and includes removal of an imaging probe from the apparatus during the procedure. Beginning at step 810, the method 800 includes delivering an apparatus, such as apparatus 100, 300, 600, or 700, through an anatomical orifice and navigating the apparatus to an anatomical target. The slidable imaging probe is configured for delivery to the treatment location within the apparatus providing for real time visualization of anatomy as the apparatus is navigated to the anatomical target site. The apparatus may be steerable or, as will be described in more detail below, the apparatus may be delivered within a separate steerable device. During delivery, information regarding the position and/or the shape of the apparatus obtained from the pressure monitor may be transmitted to the operator O using one or more elements of system 1600 and the system 1700. The pressure may indicate a potential kink in the apparatus along the length of the apparatus which may prevent a stone or stone fragment from being retrieved. Additionally, or alternatively, a shape sensing fiber integrated within the apparatus may indicate a kink. In response to information obtained from the pressure monitor, the operator O may adjust a pose of the apparatus to eliminate the kink.

At step 820, an operator O obtains location information describing the relative position and orientation of a distal end of the apparatus in relation to a target, such as a kidney stone. The location information can include information from images transmitted by the slidable imaging probe, imaging data from external imaging such as fluoroscopy or CT, or sensor data for sensors included within the apparatus or provided within the steerable device used to deliver the apparatus. In response to the location information, the operator O can advance in the distal direction, retract in the proximal direction, and or steer the steerable apparatus to a desired location relative to the treatment location. In addition, the operator O can distally advance and/or proximally retract the imaging probe independent of the steerable apparatus to obtain additional location information. Such location information is useful to avoid contacting one or more anatomical structures when delivering the steerable apparatus, determining the location of the steerable apparatus within the subject, adjusting the location of the steerable apparatus, and/or for methods of locating material from the subject to position the steerable apparatus proximate the material and for determining the location of the steerable apparatus relative to the material.

The method 800 includes optionally determining if the steerable apparatus, is, for example, located close to or at an anatomical wall or other anatomical structure, and deploying one or more standoff elements. For example, at step 830, if the apparatus is determined to be positioned close to an anatomic structure, such as a tissue wall, from step 820 above, the method 800 further optionally includes providing at least one radially deployable standoff element to space the apparatus from the tissue wall. As discussed above in greater detail with respect to FIGS. 6A 7B, one or more radially deployable standoff elements (e.g., nitinol wires) may be deployed to maintain a pose of the apparatus during delivery and/or positioning. The nitinol wire may be radially deployable from the sidewall or other portion of the surgical apparatus using an actuator or other mechanism manually, robotically, or teleoperably controlled by the operator O. In some embodiments, the operator O may maintain a pose to prevent the apparatus from contacting an anatomical structure, to retain a location of the apparatus relative to material that is intended to be suctioned, fragmented, irrigated, or otherwise removed from the subject.

At step 840, the method 800 comprises parking the apparatus at the target location. Using imaging such as endoscopic images, and external imaging such as fluoroscopy or CT, the apparatus can be oriented so that a distal face of the apparatus is pointed towards the target material, e.g. kidney stone. The position and orientation of the apparatus may be stabilized using rigidizing mechanisms as will be described in more detail below with reference to FIGS. 10A-C, or the apparatus may be stabilized within a separate steerable or non-steerable device as will be described in more detail with reference to FIGS. 17A and 17B. The method 800 may optionally include verifying position, orientation, and location of the apparatus in relation to the target stone using location information as described in reference to step 820.

At step 850, the method 800 comprises determining a size of a stone at the target location. The size of the stone may be determined by using imaging, such as endoscopic imaging, endoluminal ultrasound, OCT, fluoroscopy, CT, MRI, and/or the like. The images may be obtained as live images, may be acquired pre-operatively, or a combination of live images and per-operative images may be used.

At step 860, the method 800 comprises removing the slidable imaging probe from the first elongated channel to clear the first channel. The imaging probe can be removed by retracting the imaging probe from a proximal end of the apparatus. In some embodiments, for example, the slidable imaging probe is coupled to a motorized mechanism allowing for automatic or tele-robotic insert and removal of the imaging probe from the first elongated channel.

At step 865, the method 800 comprising comparing the determined size of the stone from step 850 to a threshold stone size. In some examples, the threshold stone size can be determined based on the size of the apparatus and thus the size of the first and/or second channels. For example, the size of the apparatus could be similar to that of a standard ureteroscope and provide for an approximate 1.2 mm working channel. Accordingly, the threshold of stone size would be under 1.2 mm. In another example, the apparatus may include a larger working channel than a standard ureteroscope given the removable slidable imaging probe and thus the threshold stone size may be in the range of 1.2 mm-2 mm. In alternative examples, the apparatus may be sized to be various French sizes, e.g. 3 Fr, 4 Fr, or 5 Fr allowing for working channels below 1-1.7 mm providing for threshold stone size in a similar range. If the determined stone size from step 850 is less than or equal to the threshold stone size, the method 800 proceeds to step 870 described below to remove the stone from the target location using suction. If the determined stone size from step 850 is greater than the threshold stone size, step 875 is performed before step 870 and, in some embodiments, steps 875 and 870 may be performed iteratively until the stone has been sufficiently fragmented below the threshold stone size and removed.

At step 870, the method 800 includes providing suction through the second elongated channel to remove material (e.g., a stone, a fragment of a stone, and/or stone dust) from the target location and simultaneously providing irrigation through the first elongated channel to increase fluid flow. In some alternative embodiments, suction can instead be provided through the first elongated channel and irrigation can instead be provided through the second elongated channel. In some embodiments, pressure or fluid flow within the channel used for suction can be measured to determine if a stone or stone fragment is lodged in the channel. A sudden pressure decrease or a sudden loss of fluid flow can indicate a lodged stone. To dislodge a stone, fluid flow can be reversed during the removal procedure, e.g., providing irrigation to one channel in which a stone is lodged and suction to the other channel.

Suction and irrigation can be applied until the stone and stone fragments have been removed. In some embodiments, fluoroscopy or intra-operative CT can be used to identify if stones or stone fragments remain. In other embodiments, pressure can be measured and a drop in pressure can be indicative of an opening of the first or second channel, which could correlate with stones and stone fragments no longer being retrieved. In some embodiments it is difficult to use external imaging or pressure to make a determination, so a pre-determined period of time can be used. Once either stones have been determined to be removed or the period of time has been completed, the method 800 can skip to step 880.

At step 875, the method 800 optionally includes fragmenting the stone that is too large for retrieval and retrieving the fragmented stone and stone dust. A tool, such as a laser fiber, can be delivered through the first elongated channel. The tool can be active, e.g., laser energy can be delivered, to fragment the stone while vacuum can be provided through the second elongated channel for retrieval. By simultaneously fragmenting and suctioning, the apparatus decreases the risk of losing fragmented stones within anatomy that could have been lost if fragmenting and suctioning were completed in two separate steps. In an alternative embodiment, the tool may be delivered within the second elongated channel and the vacuum could be provided through the first elongated channel.

Additionally, in some embodiments, irrigation could be simultaneously provided during fragmenting and suctioning, thereby increasing fluid flow. For example, the laser fiber tool may be delivered within the first elongated channel, suction may be provided through the second elongated channel, and irrigation could be provided through the first elongated channel using additional space in the first elongated channel not occupied by the laser fiber. In an alternative example, the laser fiber tool may be delivered within the second elongated channel, suction may be provided through the first elongated channel, and irrigation may be provided through the second elongated channel using additional space surrounding the laser fiber.

Fragmenting and suction (and optionally irrigation) can be applied until the stone and stone fragments have been removed. In some embodiments, fluoroscopy or intra-operative CT can be used to identify if stones or stone fragments remain. In other embodiments, pressure can be measured and a drop in pressure can be indicative of an opening of the first or second channel, which could correlate with stones and stone fragments no longer being retrieved. In some embodiments it is difficult to use external imaging or pressure to make a determination, so a pre-determined period of time can be used. Once either stones have been determined to be removed or the period of time has been completed, the method 800 can move on to step 880.

At step 880, method 800 provides for verifying whether a stone has sufficiently retrieved or has moved beyond a distance for retrieval. In step 880, the imaging probe can be replaced within the first elongated channel and used to visually determine if a stone has been adequately retrieved. If the stone is not within near proximity of the distal end of the apparatus, the method 800 can move to step 890. If the stone or stone fragments remain within a distance for retrieval, the method 800 should return to step 860.

At step 890, the method 800 comprises determining if the target stone has moved to a different location or if additional stones need to be retrieved. In some embodiments, the determination can be completed using fluoroscopic or live CT views or were determined using pre-operative CT data. In alternative embodiments the apparatus can be repositioned, by inserting, retracting, and steering the apparatus, within the kidney to search for additional stones. For example, imaging information includes a first image of the target location and a second image of at least one alternative location captured by repositioning of the slidable imaging probe or the elongated shaft. In some embodiments the apparatus is steerable, in alternative embodiments, the apparatus is passive but held within a lumen of a steerable device which can be repositioned using insertion, retraction, and steering as will be described in detail below. If it is determined that a stone or plurality of stones (e.g. a new stone or a stone fragment) require retrieval, the method 800 can return to step 820. If it is determined that there are no stones or stone fragments left for retrieval, the method 800 is complete, and the apparatus can be removed (e.g., proximally retracted) from the subject's anatomy.

FIG. 9 illustrates a simplified flow diagram of a method 900 of positioning a steerable apparatus at a treatment location for retrieval of target material from a subject. As described in further detail below, the method 900 includes opening of an elongated channel of the apparatus carrying an imaging probe by distally advancing the imaging probe past a distal face of the apparatus during the procedure.

Beginning at step 910, the method 900 includes delivering an apparatus, such as apparatus 100, 300, 600, or 700, through an anatomical orifice and navigating the apparatus to an anatomical target. The slidable imaging probe is configured for delivery to the treatment location within the apparatus providing for real time visualization of anatomy as the apparatus is navigated to anatomical target site. The apparatus may be steerable or, as will be described in more detail below, the apparatus may be delivered within a separate steerable device. During delivery, information regarding the position and/or the shape of the apparatus obtained from the pressure monitor may be transmitted to the operator O using one or more elements of system 1600 and the system 1700. The pressure may indicate a potential kink in the apparatus along the length of the apparatus which may prevent a stone or stone fragment from being retrieved. Additionally, or alternatively, a shape sensing fiber integrated within the apparatus may indicate a kink. In response to information obtained from the pressure monitor, the operator O may adjust a pose of the apparatus to eliminate the kink.

At step 920, an operator O obtains location information describing the relative position and orientation of a distal end of the apparatus in relation to a target, such as a kidney stone. The location information can include information from images transmitted by the slidable imaging probe, imaging data from external imaging such as fluoroscopy or CT, or sensor data for sensors included within the apparatus or provided within the steerable device used to deliver the apparatus. In response to the location information, the operator O can advance in the distal direction, retract in the proximal direction, and or steer the steerable apparatus to a desired location relative to the treatment location. In addition, the operator O can distally advance and/or proximally retract the imaging probe independent of the steerable apparatus to obtain additional location information. Such location information is useful to avoid contacting one or more anatomical structures when delivering the steerable apparatus, determining the location of the steerable apparatus within the subject, adjusting the location of the steerable apparatus, and/or for methods of locating material from the subject to position the steerable apparatus proximate the material and for determining the location of the steerable apparatus relative to the material.

The method 900 includes optionally determining if the steerable apparatus, is, for example, located close to or at an anatomical wall or other anatomical structure, and deploying one or more standoff elements. For example, at step 930, if the apparatus is determined to be positioned close to an anatomic structure, such as a tissue wall, from step 920 above, the method 900 further optionally includes providing at least one radially deployable standoff element to space the apparatus from the tissue wall. As discussed above in greater detail with respect to FIGS. 6A-7B, one or more radially deployable standoff elements (e.g., nitinol wires) may be deployed to maintain a pose of the apparatus during delivery and/or positioning. The nitinol wire may be radially deployable from the sidewall or other portion of the surgical apparatus using an actuator or other mechanism manually, robotically, or teleoperably controlled by the operator O. In some embodiments, the operator O may maintain a pose to prevent the apparatus from contacting an anatomical structure, to retain a location of the apparatus relative to material that is intended to be suctioned, fragmented, irrigated, or otherwise removed from the subject.

At step 940, the method 900 comprises parking the apparatus at the target location. Using imaging such as endoscopic images, and external imaging such as fluoroscopy or CT, the apparatus can be oriented so that a distal face of the apparatus is pointed towards the target material, e.g. kidney stone. The position and orientation of the apparatus may be stabilized using rigidizing mechanisms as will be described in more detail below with reference to FIGS. 10A-C or the apparatus may be stabilized within a separate steerable or non-steerable device as will be described in more detail with reference to FIGS. 17A and 17B. The method 900 may optionally include verifying position, orientation, and location of the apparatus in relation to the target stone using location information as described in reference to step 920.

At step 950, the method 900 comprises determining a size of a stone at the target location. The size of the stone may be determined by using imaging, such as endoscopic imaging, endoluminal ultrasound, OCT, fluoroscopy, CT, MRI, and/or the like. The images may be obtained as live images, may be acquired pre-operatively, or a combination of live images and per-operative images may be used.

At step 960, the method 900 comprises clearing the first elongated channel by slidably advancing the slidable imaging probe through the first elongated channel to a position where a camera head of the imaging probe is advanced past a distal face of the apparatus and the camera head has cleared the first elongated channel. In some embodiments, the slidable imaging probe is coupled to a motorized mechanism allowing for automatic or tele-robotic insertion and/or removal of the imaging probe from the first elongated channel.

At step 965, the method 900 comprises comparing the determined size of the stone from step 950 to a threshold stone size. If the determined stone size from step 950 is less than or equal to the threshold stone size, the method 900 proceeds to step 970 described below to remove the stone from the target location using suction. If the determined stone size from step 950 is greater than the threshold stone size, step 975 is performed before step 970 and, in some embodiments, steps 975 and 970 may be performed iteratively until the stone has been sufficiently fragmented below the threshold stone size and removed.

At step 970, the method 900 includes providing suction through the second elongated channel to remove material (e.g., a stone, a fragment of a stone, and/or stone dust) from the target location and simultaneously providing irrigation through the first elongated channel to increase fluid flow. In some alternative embodiments, suction can instead be provided through the first elongated channel and irrigation can instead be provided through the second elongated channel. In some embodiments, pressure or fluid flow within the channel used for suction can be measured to determine if a stone or stone fragment is lodged in the channel. A sudden pressure decrease or a sudden loss of fluid flow can indicate a lodged stone. To dislodge a stone, fluid flow can be reversed during the removal procedure, e.g. providing irrigation to one channel in which a stone is lodged and suction to the other channel.

Suction and irrigation can be applied until the stone or stone fragments have been removed, or the stone or stone fragments are no longer in retrievable distance from the distal end of the apparatus. Because the imaging probe has been positioned within patient anatomy, continuous visualization of the target site can be used to make a determination of when to discontinue suction and irrigation. Once step 970 is complete, the method 900 can skip to step 980.

At step 975, the method 900 includes fragmenting the stone that is too large for retrieval and retrieving the fragmented stone and stone dust. A tool, such as a laser fiber, can be delivered through the first elongated channel. The tool can be active, e.g. laser energy can be delivered, to fragment the stone while vacuum can be provided through the second elongated channel for retrieval. By simultaneously fragmenting and suctioning, the apparatus decreases the risk of losing fragmented stones within anatomy that could have been lost if fragmenting and suctioning were completed in two separate steps. In an alternative embodiment, the tool may be delivered within the second elongated channel and the vacuum could be provided through the first elongated channel.

Additionally, in some embodiments, irrigation could be simultaneously provided during fragmenting and suctioning, increasing fluid flow. For example, the laser fiber tool may be delivered within the first elongated channel, suction may be provided through the second elongated channel, and irrigation could be provided through the first elongated channel using additional space in the first elongated channel not occupied by the laser fiber. In an alternative example, the laser fiber tool may be delivered within the second elongated channel, suction may be provided through the first elongated channel, and irrigation may be provided through the second elongated channel using additional space surrounding the laser fiber.

Fragmenting and suction (and optionally irrigation) can be applied until the stone or stone fragments have been removed, or the stone or stone fragments are no longer in retrievable distance from the distal end of the apparatus. Because the imaging probe has been positioned within patient anatomy, continuous visualization of the target site can be used to make a determination of when to discontinue suction and irrigation. Once step 970 is complete, the method 900 can move on to step 980.

At step 980, the method 900 comprises repositioning the apparatus, by inserting, retracting, and steering the apparatus, within the kidney to search for additional stone fragments which have moved or search for additional stones. In some embodiments the apparatus is steerable, in alternative embodiments, the apparatus is passive but held within a lumen of a steerable device which can be repositioned using insertion, retraction, and steering as will be described in detail below. In some embodiments, the imaging probe is additionally steerable and can be navigated within the organ to search for stones. Once located, the apparatus can be repositioned to a location near the newly located stones or stone fragments. If it is determined that a stone or plurality of stones (e.g. a new stone or a stone fragment) require retrieval, the method 900 can return to step 920. If it is determined that there are no stones or stone fragments left for retrieval, the method 900 is complete, and the apparatus can be removed (e.g., proximally retracted) from the subject's anatomy.

As discussed above, the present disclosure is directed to apparatuses configured for, use in procedures that requires suction and/or irrigation and imaging, such as ureteroscopes for removing material at an anatomic location. It can be helpful to provide delivery methods and apparatus for effectively navigating the apparatus from the anatomic opening (e.g. a natural or artificially created orifice), through potentially tortuous anatomy, to the particular anatomic target location. In one embodiment, it can be helpful to provide partial, variable, or selective rigidization of the apparatus as it is advanced through anatomy. In other embodiments, the apparatus may be delivered using a separate steerable sheath, for example a robotically steerable instrument.

Figure 10A:
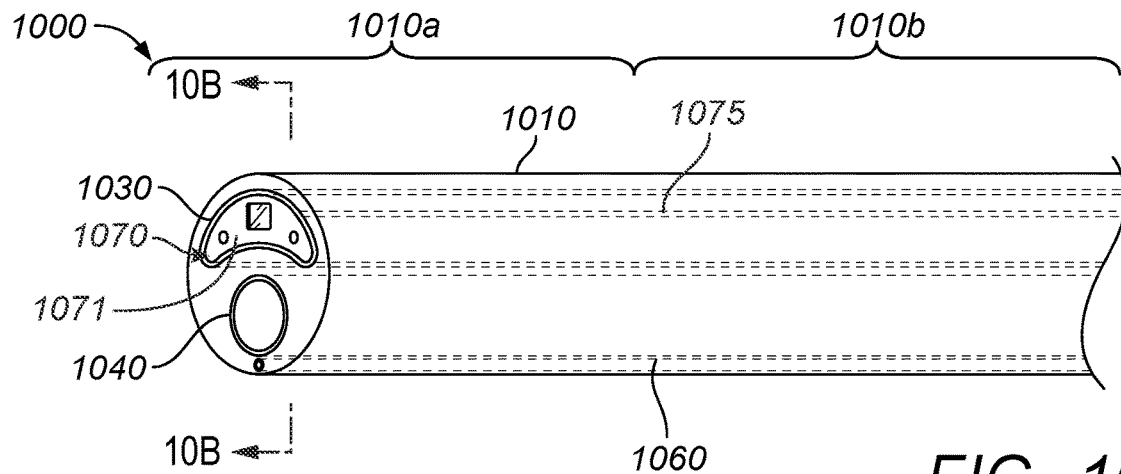
FIG. 10A illustrates a portion of an apparatus, such as a medical instrument, configured in accordance with further embodiments of the present technology.
Figure 10B:
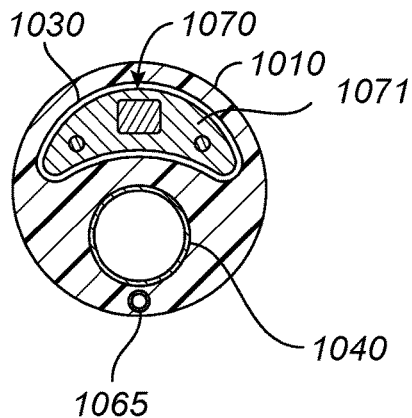
FIG. 10B is a cross-sectional view taken along line 10B-10B of FIG. 10A.
Figure 10C:
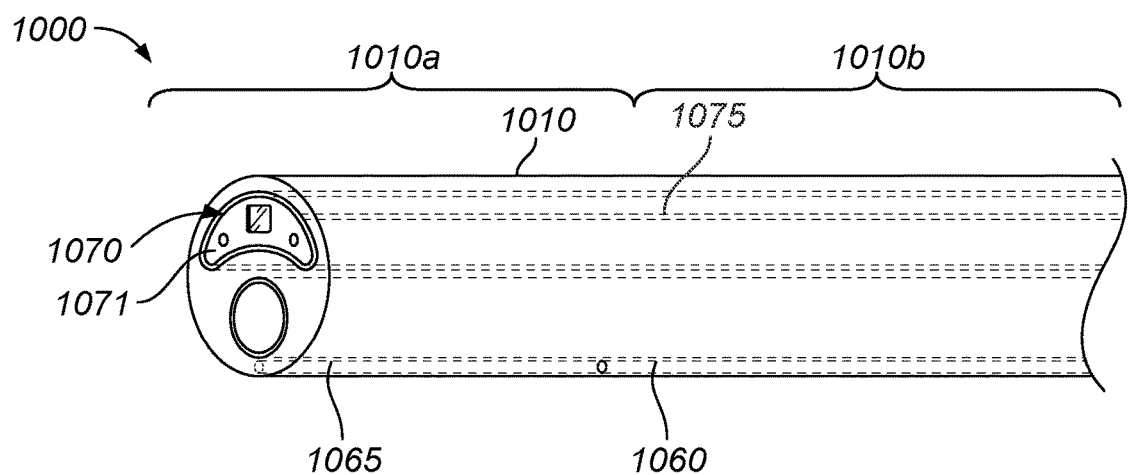
FIG. 10C illustrates a portion of an apparatus, such as a medical instrument, configured in accordance with further embodiments of the present technology.

FIGS. 10A and 10C illustrate a portion of another steerable apparatus 1000 configured in accordance with various embodiments of the present technology. FIG. 10B is a cross-sectional view taken along line 10B-10B of FIG. 10A. Unless noted otherwise and regardless if illustrated in FIGS. 10A-10C, the apparatus 1000 includes elements, features, and configurations that are generally similar to those, or the same as those, of the apparatuses 100, 300, 500, 600, and 700 described herein. Referring to FIGS. 10A and 10B together, the apparatus 1000 includes a shaft 1010 and an elongated spine 1060 ("rigidizable spine 1060") configured to be actively stiffened. The rigidizable spine 1060 can be positioned within the shaft 1010, extending from a distal portion 1010a to a proximal portion 1010b of shaft 1010, and, as shown in FIG. 10A, may extend to a distal tip of the apparatus 1000.

As shown in FIG. 10C, the rigidizable spine 1060 is slidable and can be retracted proximally through a sidewall lumen 1065 or extended distally past the distal portion 1010a (not shown). While the rigidizable spine 1060 is illustrated adjacent to a second elongated channel 1040 and disposed within the shaft 1010, in other embodiments the rigidizable spine 1060 may also be positioned adjacent to a first elongated channel 1030 of the shaft 1010 between the first elongated channel 1030 and the second elongated channel 1040, or positioned within the first elongated channel 1030 and the second elongated channel 1040. In some embodiments, multiple rigidizable spines 1060 may be disposed within the shaft 1010, adjacent the first elongated channel 1030, adjacent the second elongated channel 1040, between the first elongated channel 1030, positioned within the first elongated channel 1030 and/or positioned within the second elongated channel 1040.

In some embodiments, the second elongated channel 1040 may be decoupled from the apparatus 1000 and slidable along a length of the apparatus, such as distally from the proximal portion 1010b of the shaft 1010 toward the distal portion 1010a, proximally from the distal portion 1010a of the shaft 1010 toward the proximal portion 1010b, or a combination thereof. In the decoupled configuration, the second elongated channel 1040 may be positioned to extend distally from the distal portion 1010a of the shaft 1010 or retracted proximally from the distal portion 1010a of the shaft 1010 in order to act as a guide rail around bends as will be described in further detail below. In addition to, or in lieu of, the rigidizable spine 1060, the second elongated channel 1040 may itself be rigidizable and/or the first elongated channel 1030 may be rigidizable. In some embodiments, the first elongated channel 1030 and/or the second elongated channel 1040 may be decoupled from the apparatus 1000 and slidable along a length of the apparatus.

In some embodiments, a slidable imaging probe 1070, which is similar in structure and function as slidable imaging probe 170/570, includes a camera head 1071 and a cable assembly 1075. However, cable assembly 1075 can additionally include a sheath or mechanism which provides for active rigidization, allowing for the cable assembly 1075 to be controllably placed in either a rigid or relaxed state. The slidable imaging probe 1070 can extend distally from the distal portion 1010a of the shaft 1010 or retracted proximally from the distal portion 1010*a* of the shaft 1010 in order to act as a guide rail around bends as will be described in further detail below.

Figure 11A:
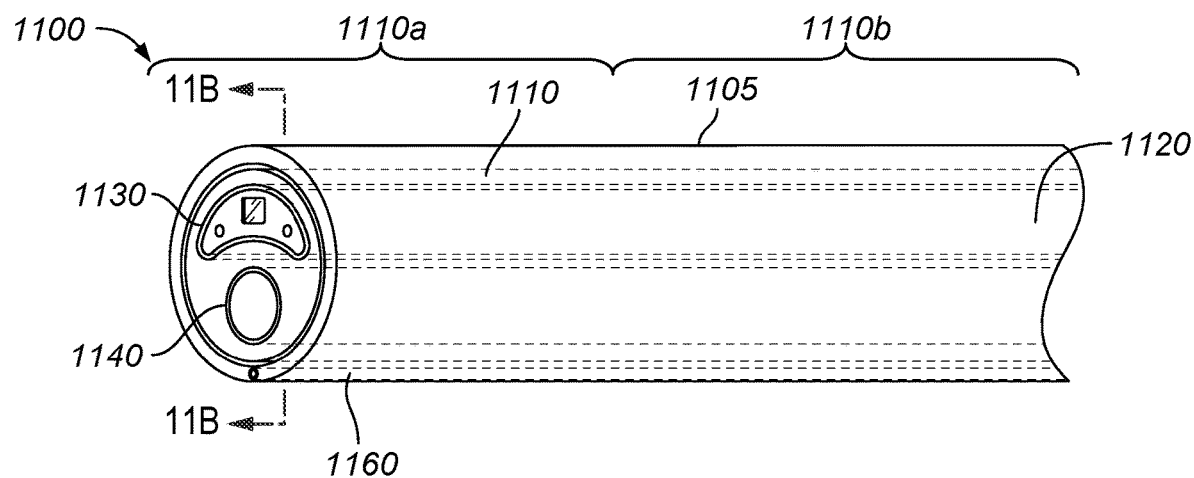
FIG. 11A illustrates a portion of an apparatus, such as a medical instrument, configured in accordance with embodiments of the present technology.
Figure 11B:
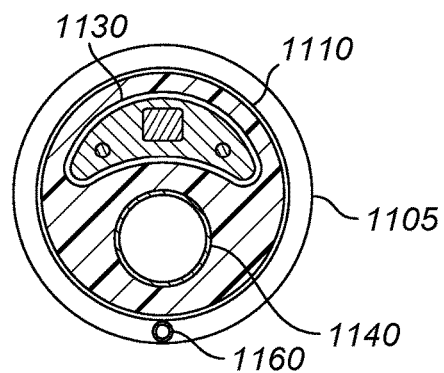
FIG. 11B is a cross-sectional view taken along line 11B-11B of FIG. 11A.

FIG. 11A illustrates a portion of another apparatus 1100 configured in accordance with various embodiments of the present technology, and FIG. 11B is a cross-sectional view taken along line 11B-11B of FIG. 11A. Referring to FIGS. 11A and 11B together, the apparatus 1100 includes a rigidizable spine 1160 disposed between an exterior region of the sidewall 1120 of shaft 1110 and an inner surface of access sheath 1105. In some embodiments, access sheath 1105 may be passive, manually steerable, or robotically steerable as will be described in detail below. In these and other embodiments, a stiffness or rigidity of the access sheath 1105 can be uniform or can vary in a manner consistent with the discussion of the elongated shaft 110 of FIG. 1A above (e.g., by varying material compositions, material durometers, shaft or material dimensions, cut out dimensions, cut out spacings, etc.).

Similar to the rigidizable spine 1060 described above with reference to FIGS. 10A and 10B, the rigidizable spine 1160 is configured to be stiffened from a relaxed conformation into a rigidized conformation or relaxed from a rigidized conformation. While the rigidizable spine 1160 is illustrated adjacent to a second elongated channel 1140 of the apparatus 1100, the rigidizable spine 1160 may also be positioned at alternative locations between an exterior region of the sidewall 1120 and an inner surface of the access sheath 1105, or within a lumen within a wall of the access sheath 1105. Similar to rigidizable spine 1060, the rigidizable spine 1160 may be decoupled from the apparatus 1100 and slidable along a length of the apparatus, such as distally from the proximal portion 1110*b* of the shaft 1110 toward the distal portion 1110*a*, proximally from the distal portion 1110*a* of the shaft 1110 toward the proximal portion 1110*b*, or a combination thereof. It will be appreciated that even when in a decoupled and/or rigidizable configuration, the second elongated channel 1140 may be configured for irrigation, suction, and/or carrying one or more removable tools.

Various suitable mechanisms and materials may be used to rigidize selected features of the apparatuses described herein. Without intending to be limiting, suitable mechanisms include heat, electricity (e.g., nitinol), vacuum, pressure, tension (e.g., a pull wire), etc. For example, rigidizable mechanisms may also include a pressure system that increases pressure or vacuum to rigidize and decreases pressure or vacuum to relax a shape of the apparatus, in addition to or instead of nitinol actuators or other rigidizable mechanisms. In addition, the first elongated channel or the second rigidizable channels can each be rigidizable using fluid flow from the fluid circulation apparatus. Pressure systems can include, but are not limited to, a channel connected to irrigation such that when fluid is provided within the channel increasing pressure within the channel, the channel and thereby the apparatus, rigidizes (e.g., stiffens). In some embodiments, the channel includes an actuated seal to ensure providing pressure is effective. In other embodiments of the channel including the actuated seal, vacuum can be used to rigidize instead of pressure. As another example, rigidizable mechanisms may include, but are not limited to, nitinol actuators extending within a wall structure of the flexible elongated shaft 1010 or shaft 1110. Selectively activating the rigidizable mechanisms includes actuating/energizing at least one of the plurality of nitinol actuators. These rigidizable mechanisms may be part of a steering mechanism (not shown), may be separately actuated and/or may themselves also enable steering of the apparatus 1000 or apparatus 1100. Various rigidizable mechanisms related to rigidizable devices and apparatuses are described in PCT Pub. No. 2019/246240 (filed Jun. 19, 2019, titled "Systems and Methods for Safe Operation of a Device")

In some embodiments where the first elongated channel 1030/1130 and/or second elongated channel 1040/1140 are decoupled from the apparatus 1000/1100, the first and second elongated channels 1030/1130/1040/1140 can be extended distally beyond a distal end of the shaft 1110 to increase fluid flow, airflow, or a combination thereof around or within the apparatus 1100. When configured with decoupled channels, such as the first elongated channel 1030/1130 and/or second elongated channel 1040/1140, the apparatus 1000/1100 can be used to reach material positioned too far for an apparatus not having decoupled channels to reach. For example, the first elongated channel 1030/1130 and/or the second elongated channel 1040/1140 can be decoupled from the apparatus 1000/1100 and extended distally to remove the material if the apparatus 1000/1100 otherwise could not be distally advanced to the material. As another example, the first elongated channel 1030/1130 and/or the second elongated channel 1040/1140 can also be configured as a support structure (e.g., a rail) for the apparatus 1000/1100, an access sheath (not shown), and/or one or more removable tools.

Figure 12:
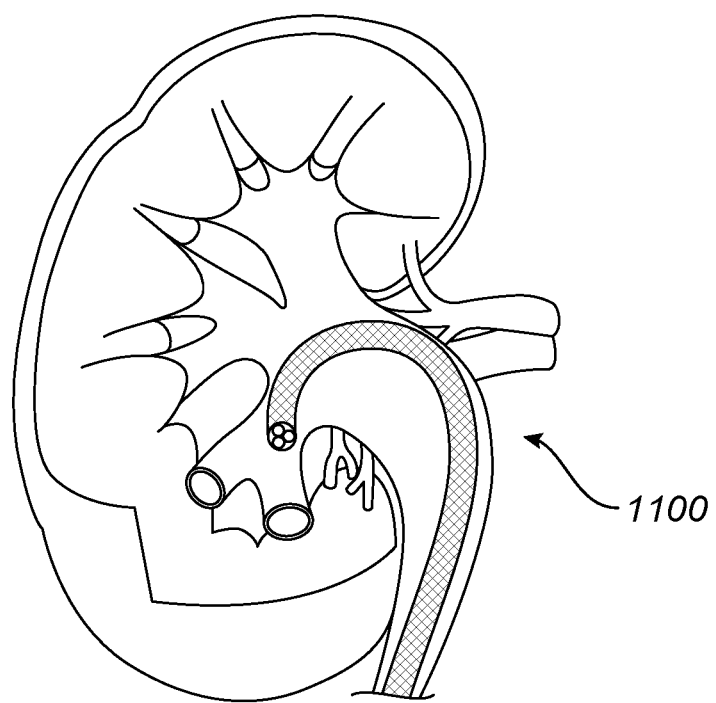
FIG. 12 illustrates a portion of an apparatus, such as a medical instrument, configured in accordance with additional embodiments of the present technology and disposed within a kidney of a human patient.

During operation, the rigidizable feature(s), such as the rigidizable spine 1060, the first elongated channel 1030, the second elongated channel 1040, the slidable imaging probe 1070, the rigidizable spine 1160, and other rigidizable features may assist or enable advancing the steerable apparatuses through a subject's anatomy, especially within an organ, as disclosed herein. For example, as an apparatus is advanced into a kidney through an anatomical orifice, such as a subject's ureter, as illustrated in FIG. 12, the apparatus is navigated through a large chamber. If the target stone to be accessed is at a location in the lower portion of the kidney, the apparatus must make a tight bend turn as it is being positioned toward the material at the target location. With delivery and/or positioning of flexible devices such as catheters or ureteroscopes, an intermediate length of the ureteroscope may move towards the wall of the renal pelvis. In this way, insertion from a proximal end of the apparatus results in a distal end of the apparatus retracting instead of inserting as the intermediate portion of the instrument continues to press against the renal pelvis wall. Delivery of conventional ureteroscopes is therefore not intuitive as forward commanded motion from the operator at the proximal end of the instrument results in a perceived retraction of the distal end of the instrument. Not only does delivery of conventional ureteroscopes result in inefficiencies due to perceived retraction, but the conventional ureteroscopes contact at least a portion of an anatomical structure within the subject which may cause damages. Thus, rigidizable features such as the rigidizable spine 1060/1160, first elongated channel 1030, and the second elongated channel 1040 may be included in apparatuses of the present disclosure to address these problems with conventional ureteroscopes.

Figure 13A:
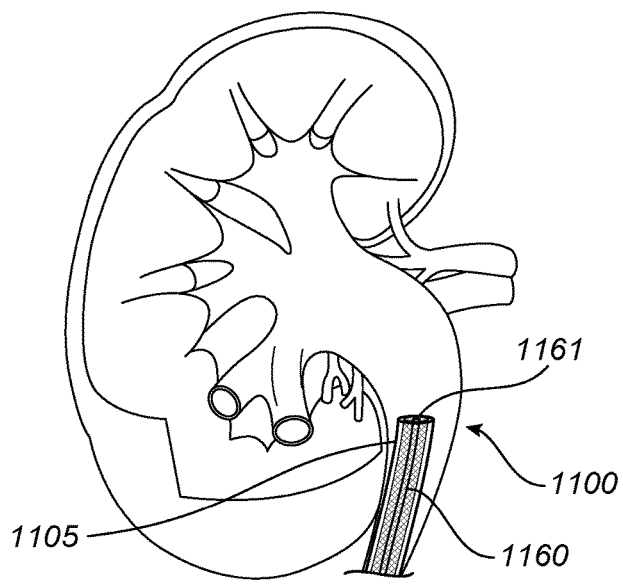
FIGS. 13A-13C illustrates a portion of an apparatus, such as a medical instrument, configured in accordance with additional embodiments of the present technology and disposed within a kidney of a human patient.
Figure 13B:
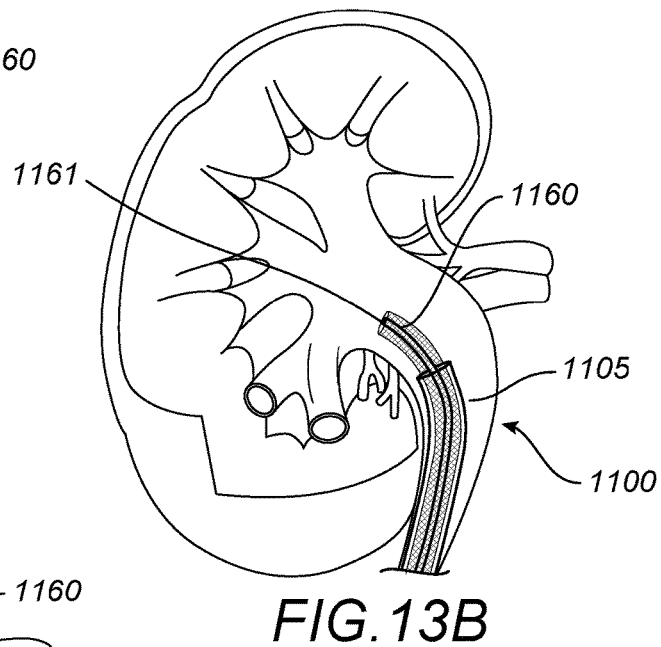
Figure 13C:
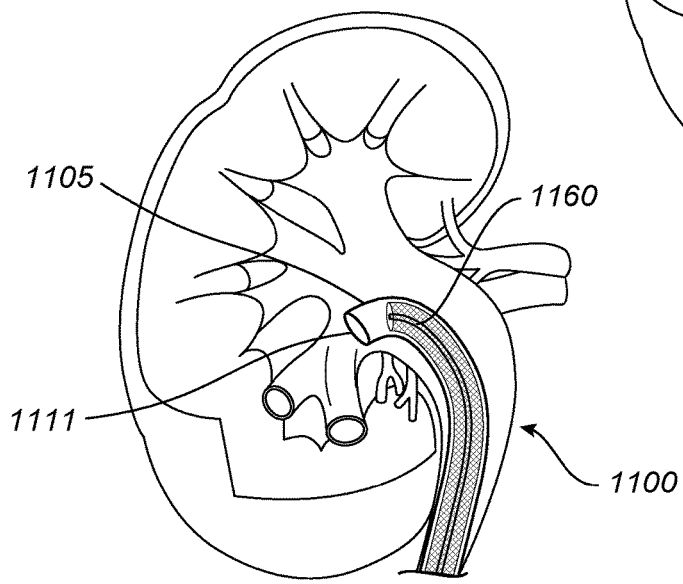

FIGS. 13A-13C illustrate how a rigidizable spine 1160 can be used to overcome the problems illustrated in FIG. 12. Referring to FIG. 13A, an apparatus 1100 having an access sheath 1105 and a rigidizable spine 1160 is advanced towards a first bend with the rigidized spine 1160 in a relaxed state. As the apparatus 1100 approaches the first bend (as illustrated in FIG. 13B), the rigidizable spine 1160 can be placed in a stiffened/rigidized state. The access sheath 1105 can be further advanced while the rigidized spine 1160 remains in the same position and orientation (as illustrated in FIG. 13C), thereby acting as a rail guiding the access sheath 1105 in a curved direction around the bend. If the apparatus 1100 is advanced to an additional bend (not shown) or requires small iterative advancements around the first bend, the rigidizable spine 1160 may be relaxed, advanced along the access sheath 1105 while the access sheath 1105 position and orientation is held stationary until a distal tip 1161 (FIG. 13A) of the rigidizable spine 1160 is flush with or slightly advanced past an apparatus distal end 1111 (FIG. 13C). The rigidizable spine 1160 can then be placed in a stiffened state and held in a stationary position and orientation while the access sheath 1105 is further advanced. The steps can be iteratively repeated until the apparatus 1100 has adequately navigated any further bends before reaching the targeted stone.

In some embodiments, the rigidizable mechanisms may use information from sensor systems to determine which portion of the elongated shaft may be reaching a bend, drifting away from a target location, moving toward an organ wall, and/or the like, to help determine longitudinal positioning of the rigidizable mechanism along the length of the elongated shaft. If the sensors obtain such information, advancement of the apparatus may be stopped or adjusted. As will be described in more detail below, the rigidizable mechanism can be relaxed and/or advanced through the apparatus in a relaxed state to be flush or distal to the distal end of the apparatus, and rigidized. These steps can be repeated if or when the apparatus reaches the bend, drifts away from the target location, moves toward the renal wall, or the like.

The sensor systems can include any combination of pressure sensors along the length of the elongated shaft, shape sensors (e.g., fiber shape sensor or a plurality of electromagnetic sensors) in the form of optical fibers running the length of the apparatus 1000/apparatus 1100 or a plurality of electromagnetic sensors distributed along the length of the apparatus 1000/apparatus 1100, and/or a plurality of force sensors distributed along the length of the apparatus 1000, apparatus 1100. In one example, the first elongated channel 1130 or the second elongated channel 1140 can further include, or be operably coupled to either directly or indirectly, a pressure monitor (not shown). Irrigation fluid can be provided within elongated channel 1130/1140 or an actuated seal can be provided within channel 1130/1140 and vacuum could be applied. The pressure monitor can be configured to measure and provide feedback to a user ("operator O"; see FIG. 16) regarding a change in pressure indicating pressure from contact with an anatomical structure, such as an organ wall.

Sensor data can be used to position rigidizing elements within the elongated shaft. In one example, force or pressure may be measured to determine contact with an organ wall, such as the renal wall. If force or pressure is detected above a defined threshold, a rigidizing element can be inserted within elongated shaft until the force or pressure measurement decreases below a threshold by providing the elongated shaft with structure to be used to guide apparatus 1000/1100 away from the organ wall. In another example, the feedback from the pressure monitor may be combined with shape information from the shape sensor to identify a contact location between a length of the apparatus and a length of the organ wall. In this example, the rigidized element may be inserted into the apparatus and advanced to the contact location thereby providing a rail from the proximal portion along the length of the apparatus to the contact location. In yet another example, a location of a bend in the anatomical structure can be determined to provide information for positioning of the rigidizing element to act as a rail. For example, the navigation system may include fluoroscopic imaging data which may be provided to the operator O to identify a location of a bend in the anatomical structure. In addition, fluoroscopic data provided to the operator O may inform the operator O if the apparatus is advanced or retracted from the bend. In a further example, shape information and anatomical information may be provided to the operator O to determine an insertion length of the apparatus to the bend. In this example, anatomical information may be obtained pre-operatively, during a procedure, or determined based on anatomical data from a population of subjects, such as an average anatomical data. In addition, shape information may be collected during the procedure and transmitted to the operator O such that the operator O may determine if the apparatus shape has changed thereby indicating a change in position relative to the bend.

Figure 14:
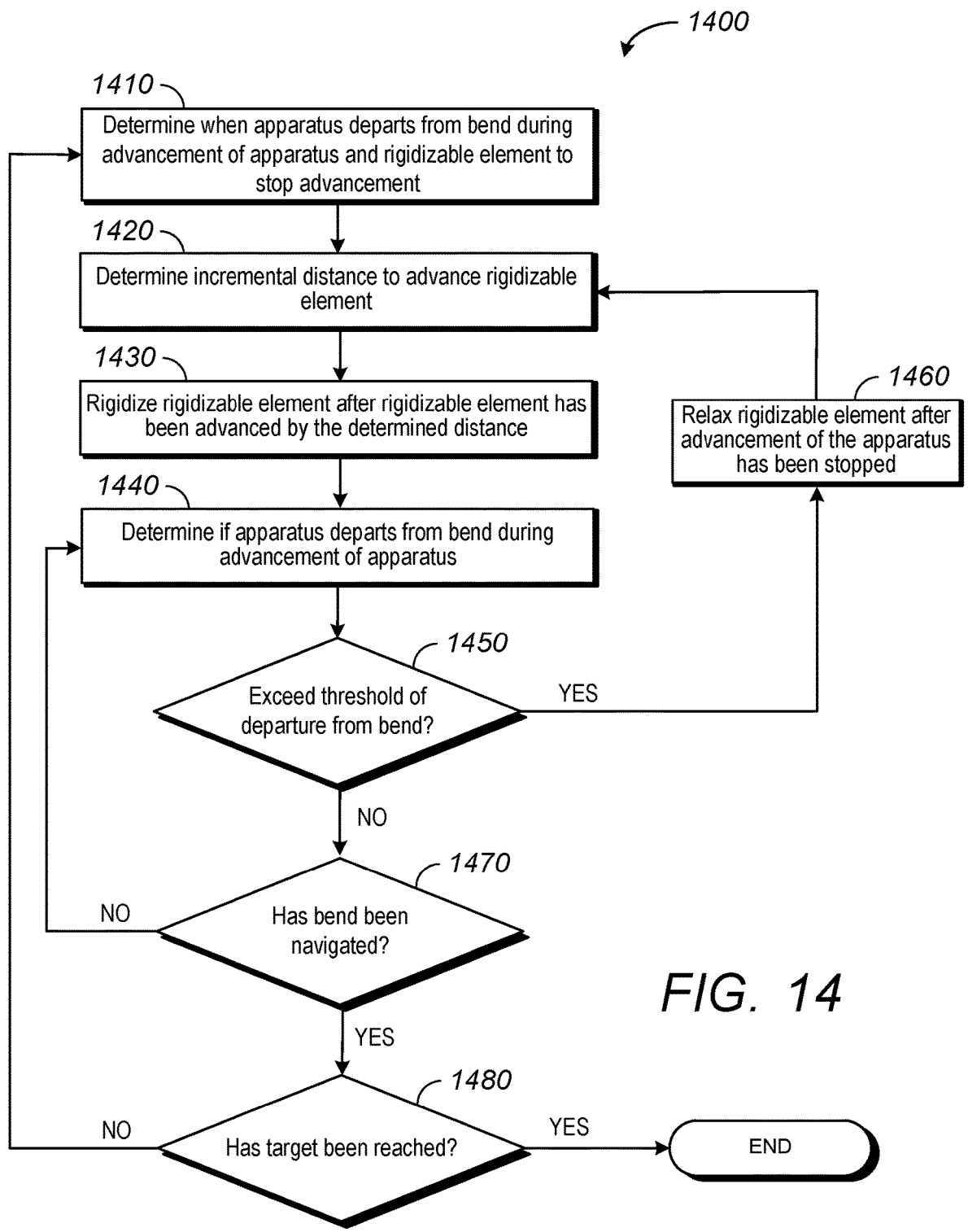
FIG. 14 is another simplified flow diagram of a method for delivering an apparatus having a rigidizable mechanism, such as a medical instrument, to a subject in need thereof in accordance with embodiments of the present technology.

FIG. 14 provides for a method 1400 for advancing an apparatus with a slidable, rigidizable element through a hollow organ. For illustration, the method 1400 is described using apparatus 1000 or 1100 of FIGS. 10A-C and 11A-B respectively, but it should be understood that method 1400 may be used for any apparatus with any slidable rigidizable element. All or a subset of the steps of the methods described herein can be executed by various instruments, apparatuses, devices, components thereof, components or devices of a robotic or teleoperated system, such as the apparatus 1000 or 1100 illustrated in FIGS. 10A-C and 11A-B, respectively and the system 1600 and the system 1700 illustrated in FIGS. 16, 17A, and 17B or other suitable apparatus or systems. Additionally, or alternatively, all or a subset of the steps of the method can be executed automatically by a processor and/or by an operator (e.g., a physician, a user, etc.) of various instruments, apparatuses, devices, components thereof, components or devices of a robotic or teleoperated system, such as the system 1600 and the system 1700 illustrated in FIGS. 16, 17A, and 17B or other suitable systems. For example, a system for delivery of an elongate shaft along a path to a target can comprise a processor communicatively coupled to the elongated shaft and the rigidizable element. In some embodiments, the processor is configured to receive information during advancement of the elongated shaft towards the target, wherein the information includes imaging information, detect a departure from a bend along the path based on the received information, determine an incremental distance to advance the rigidizable element beyond the distal end of the elongated shaft, relax the rigidizable element during advancing of the rigidizable element, rigidize the rigidizable element after the rigidizable element has been advanced the incremental distance, and/or detect completion of navigation around the bend after advancing the elongated shaft over the rigidizable element. In certain embodiments, the processor is further configured to determine a radius of the bend based on the imaging information. For example, the detecting of the departure from the bend is based on the radius. Furthermore, any one or more of the steps of the method can be executed in accordance with the discussion above.

Method 1400 provides for an incremental method to navigate an apparatus to a target within anatomy that includes at least one bend. As described in reference to FIGS. 12-13, it can be desirable to navigate the apparatus along an inner curve of a tight bend (e.g., having a small radius). Thus, in some examples, upon reaching a bend, the apparatus will be initially positioned at the bend at varying insertion locations depending on the severity of the bend, e.g. how tight or sharp the bend. Accordingly, during advancement of the apparatus, such as apparatus 1000 or 1100, toward the treatment location, beginning at step 1410, the method 1400 includes detection of a departure (veering away) from travel along the inner curve of a bend in the anatomy. When the apparatus begins to veer away from the inner curve within the bend, the advancement of the apparatus can be stopped, and the apparatus can be positioned at the bend. The detection can be determined by measuring the movement of the apparatus and determining when the apparatus has departed from the bend by a threshold amount that can be pre-determined or evaluated by the operator in real time. The movement of the apparatus can be measured using any number of sensors as previously described above. For example, intra-operative images can be used to determine if the apparatus is departing from the curve by a threshold distance from the inner curve as visualized by the operator in intra-operative images (such as CT or fluoroscopic images), or by software using imaging analysis. In another example, the departure from the threshold distance can be determined using endoluminal imaging, such as ultrasound or OCT probes integrated with or carried by the apparatus, to measure a real time distance of the apparatus to a tissue wall, e.g. the tissue wall at the inner curve. In further examples, force or pressure in combination with shape sensing can be used to detect loss of contact by a threshold force/pressure amount at a specific location along a length of the apparatus with the inner curve. In yet another example, shape sensors can be used to detect a departure of measured shape of the apparatus along the bend with determined radius of curvature of the bend as determined in pre-operative or intra-operative images. In other examples, a pre-operative model of anatomy can be rendered from pre-operative imaging data (e.g. CT data), the apparatus can use localization sensing such as shape sensing to register the apparatus to the model, and the real time position of the apparatus using the location sensing can be used to indicate when the apparatus veers from the bend within the model. The apparatus may be steerable or delivered within a separate steerable device. For example, a flexible elongated shaft, such as flexible elongated shaft 1010 or 1110 and/or an access sheath, such as the access sheath 1105 may each or all be independently steerable. In the example using an access sheath, both the access sheath and the apparatus can be positioned together in the manner described above.

Step 1410 can include disposing, advancing, and positioning a rigidizable element, in a relaxed configuration within the apparatus (e.g. within the flexible elongated shaft or the access sheath). The rigidizable element can be the rigidizable spine 1060/1160, rigidizable channel 1030/1130 or 1040/1140, or slidable imaging probe 1070/1170. In one example, the rigidizable element can be initially disposed within the apparatus and advanced together with the apparatus as it is positioned at the bend. For example, the rigidizable element, in a relaxed state, may be positioned so that a distal end of the rigidizable element is at or near a distal end of the apparatus, or at an intermediate position along the length of the apparatus then both the rigidizable element and apparatus are advanced simultaneously to the bend. If the rigidizable element is a slidable imaging probe or a rigidizable channel carrying a sliding imaging probe, it can be desirable to position the rigidizable element at least flush with the distal tip of the apparatus such that endoscopic vision can be provided to the operator O during delivery of the steerable apparatus. In other examples, the rigidizable element, in a relaxed state, may be inserted within the apparatus after the apparatus has been positioned at the first bend. The rigidizable element may be inserted to be at or near a distal end of the apparatus, or at an intermediate position along the length of the apparatus.

In order to effectively navigate the bend, the method 1400 can continue incrementally advancing until the bend is fully navigated. At step 1420, the method 1400 includes determining an incremental distance beyond the distal end of the apparatus. The incremental distance can vary based upon one or more dimensions of the bend that the operator O is navigating during delivery of the apparatus. For example, if the bend is tight, then the incremental distance is less than an incremental distance if the bend had a larger radius. The incremental distance can be determined by the operator O while the apparatus is being delivered, advanced, or otherwise positioned, or the incremental distance can be determined before performing method 1400 or step 1420 of method 1400. For example, the radius of the bend can be determined using pre-operative or live intra-operative imaging data, automatically by software image recognition techniques and/or by operator recognition and input/adjustment into software by the operator O. A processor of system 1600 or 1700 can be configured to receive data for determining one or more incremental distances.

At step 1430, the method 1400 includes rigidizing the rigidizable element of the selectively rigidizable apparatus after the rigidizable element has been advanced the incremental distance determined in step 1420. The rigidizable element can remain in a relaxed state during advancement then rigidized after being advanced the incremental distance. The advancement of the rigidizable element can be manual, motorized and controlled by operator input devices, and/or automatically robotically actuated.

At step 1440, the method 1400 includes determining if the apparatus departs from the bend while the apparatus is advanced over the rigidizable spine including holding a current insertion position of the rigidizable element in a rigid state while extending the distal end of the apparatus past the distal end of the rigidizable element. The determination of departure from the bend can be performed in a similar manner as with step 1410. For example, the detection can be determined by measuring the movement of the apparatus and determining when the apparatus has departed from the bend by the threshold amount established in step 1410. The movement of the apparatus can be measured using any number of sensors as previously described above including intra-operative or pre-operative imaging, endoluminal imaging probes, shape sensors, pressure sensors, and/or force sensors. For example, the pre-operative or intra-operative imaging can be used to determine if the apparatus is departing from the curve by the threshold amount set by the operator or by software using imaging analysis, force or pressure in combination with shape sensing can be used to detect loss of contact with the inner curve by the threshold amount, and/or shape sensors can be used to detect a departure from a curve by the threshold amount as measured in pre-operative or intra-operative images.

At step 1450, the method 1400 includes a decision step after detecting if the apparatus departing from the bend or veering from the inner curve of the bend by the threshold amount that can be pre-determined or evaluated by the operator in real time. If departure from the bend is detected, i.e. if the movement away from the bend exceeds the threshold amount, the method 1400 can proceed to step 1460 which includes relaxing the rigidizable element of the apparatus after ceasing advancement or movement of the apparatus. The insertion actuation of the apparatus can be manual, motorized and controlled by operator input devices, and/or automatically robotically actuated. The method 1400 then returns to step 1420 including advancing the rigidizable element by a distance as detailed in step 1420.

In step 1450, if the departure from the bend is not detected, method 1400 continues to step 1470 with determining whether the bend has been successfully navigated, i.e. determining if the apparatus has distally advanced past the bend. The determination can be made using similar sensors and techniques as described with reference to step 1410. In some examples, the determination can be made by the operator by using intra-operative images to visually determine that a bend has been successfully navigated. In another example, shape sensing can be used to determine if the apparatus is traveling in a substantially straight trajectory determined within a range of trajectories. In yet another example, endoluminal imaging or force/pressure sensors can be used with shape sensing to determine that an apparatus is within a threshold distance from an anatomical wall or within a threshold contact (force/pressure threshold) and the apparatus is traveling in a substantially straight trajectory which would indicate a successful navigation of the bend. If the apparatus has not distally advanced past the bend, the method 1400 includes repeating steps 1440 to 1450 until the apparatus has distally advanced past the bend at which point the method 1400 continues to step 1480.

At step 1480, the method 1400 includes determining the selectively rigidizable apparatus has reached the target location. As previously described, the determination of reaching the target location can be by detecting the target using live intra-operative imaging (e.g. fluoroscopy, CT, external ultrasound), tracking of the apparatus using localization sensors registered to a pre-operative model, live endoluminal imaging (e.g. endoluminal ultrasound, or OCT). If the selectively rigidizable apparatus has reached the target location, the method 1400 is complete. If the selectively rigidizable apparatus has reached the target location and another bend is disposed between the bend and the target location, the method 1400 includes repeating steps 1410 to 1490 until the apparatus is positioned at the target.

Collectively, the methods are telescoping methods of delivering the steerable apparatus to the subject using selectively (e.g., spatially and temporally) rigidizable portions of the steerable apparatus. Any of the foregoing steps can be performed for any duration of selective rigidization. In some embodiments, the selectively rigidizable portions of the steerable apparatus comprise, or consist of, about 10%, about 20%, about 30%, about 40%, about 50%, about 60%, about 70%, about 80%, about 90%, or about 95% of a length of the selectively rigidizable portion. In some embodiments, the selective rigidization can occur for microseconds, milliseconds, seconds, minutes, or hours. Various systems and methods related to rigidizable devices and apparatuses are described in PCT Pub. No. 2019/246240 (filed Jun. 19, 2019, titled "Systems and Methods for Safe Operation of a Device"), and U.S. Patent Pub. No. 2019/0029770 (filed Jun. 19, 2019, titled "Systems and Methods for Holding a Flexible Elongate Device in a Pose"), which are both incorporated by reference herein in their entireties.

In any of the embodiments disclosed herein, other features of the apparatuses may be rigidizable, such as selectively and/or temporally rigidizable. For example, in some embodiments at least a portion of the first channel, at least a portion of the second channel, at least a portion of the sidewalls of the shaft, or a combination thereof, may be rigidizable (selectively and/or temporally). Additionally, various features or certain portions of features of the apparatuses described herein may be independently rigidizable from each other. For example, a portion of a first channel may be selectively rigidizable relative to other portions of the first channel, or a portion of the shaft may be rigidizable relative to the first and second channels therethrough. In another example, a proximal portion of the probe may be selectively or fully rigidizable. For example, referring back to FIGS. 1A and 5, a proximal portion 175 of imaging probe 170 and an elongated body 575 of imaging probe 570 may be actively selectively rigidizable or actively fully rigidizable. Additionally, it will be appreciated that the rigidizable mechanisms and features described herein are an optional component that may not be included in all embodiments of the disclosed apparatuses.

Figure 15A:
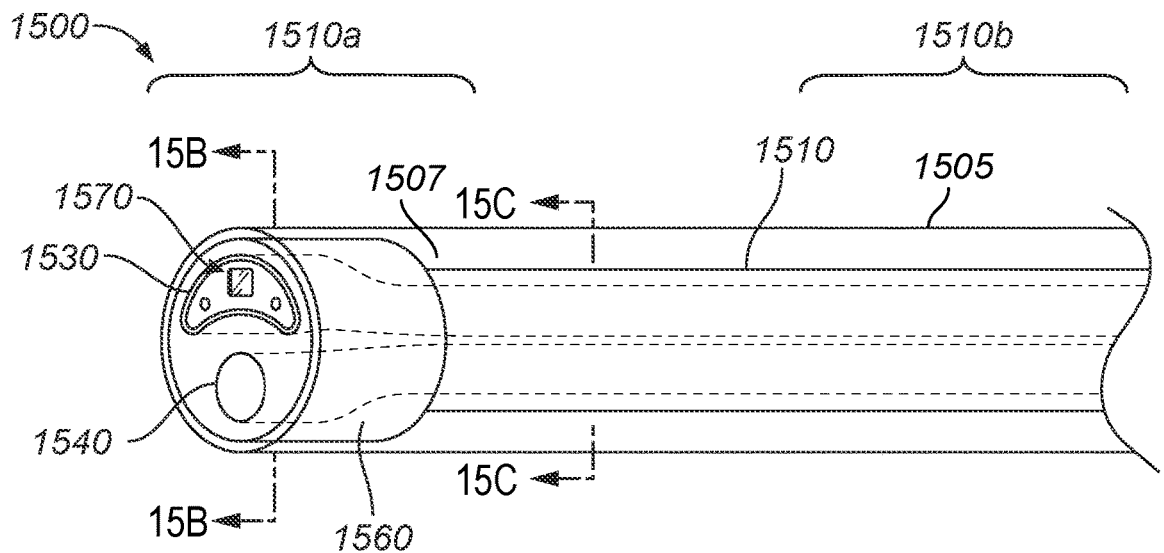
FIG. 15A illustrates a portion of an apparatus, such as a medical instrument, configured in accordance with embodiments of the present technology.
Figure 15B:
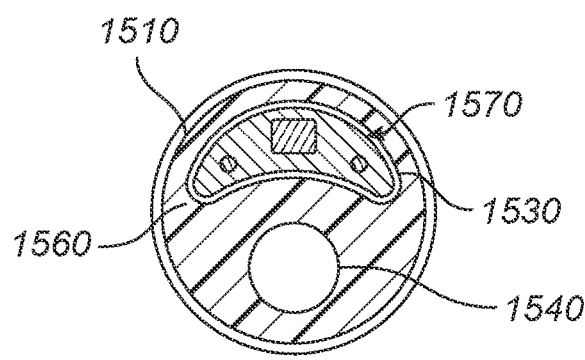
FIG. 15B is a cross-sectional view taken along line 15B-15B of FIG. 15A.
Figure 15C:
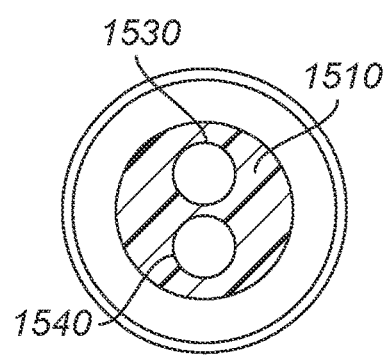
FIG. 15C is a cross-sectional view taken along line 15C-15C of FIG. 15A.

FIG. 15A illustrates a portion of another steerable apparatus 1500 configured in accordance with various embodiments of the present technology. FIGS. 15B and 15C are cross-sectional views taken along lines 15B-15B and 15C-15C of FIG. 15A, respectively. Unless noted otherwise and regardless if illustrated in any of FIGS. 15A-15C, the steerable medical apparatus 1500 includes elements, features, and configurations that are generally similar to those, or the same as those, of the apparatuses 100, 300, 500, 600, 700, 1000, 1100, and 1200 described herein. For example, a stiffness or rigidity of an access sheath 1505 of the apparatus 1500 can be uniform or can vary in a manner consistent with the discussion of the elongated shaft 110 of FIG. 1A above (e.g., by varying material compositions, material durometers, shaft or material dimensions, cut out dimensions, cut out spacings, etc.).

Referring to FIGS. 15A-15C together, the apparatus 1500 comprises an elongated shaft 1510 with a first channel 1530 and a second channel 1540. The apparatus 1500 further includes a head 1560 at a distal zone 1510a of elongated shaft 1510 with a first diameter greater than a diameter of a proximal zone 1510b of the shaft 1510. When disposed within the access sheath 1505, the "stepped-down" configuration of the apparatus 1500 creates space that defines a lumen 1507 between the elongated shaft 1510 and an inner face of the access sheath 1505. The lumen 1507 may increase a flow rate for fluid (e.g., irrigation) within the lumen surrounding the apparatus 1500 within the access sheath resulting in improved irrigation compared to apparatuses that are not configured in a stepped-down arrangement. When configured as illustrated in FIGS. 15A-15C, apparatus 1500 may have enhanced trackability of the elongated shaft 1510 within the access sheath and/or may be positioned in the absence of the access sheath. In either configuration (e.g., with or without the access sheath), the stepped-down configuration provides additional space between the elongated shaft 1510 and the inner face of the access sheath 1505 or the anatomical structure for fragments of material to pass during removal.

As shown, the first channel 1530 and the second channel 1540 each have a diameter generally similar to a diameter of the first elongated channel lumen and the second channel lumen. In other embodiments, however, the first channel opening and the second channel opening may have a diameter greater than (or less than) a diameter of the first channel lumen and the second channel lumen. In the illustrated configuration, an imaging probe 1570 is configured to be advanced distally from the head 1560 rather than proximally through the elongated shaft 1510. Once the imaging probe has been distally advanced a sufficient distance away from the head 1560, the first channel 1530 is open and available for suction, irrigation, or a combination thereof. Similar to other apparatuses described herein, apparatus 1500 may be manually, robotically, and/or teleoperably operated, and/or may be disposed within an access sheath that is manually, robotically, and/or teleoperably operated.

Figure 16:
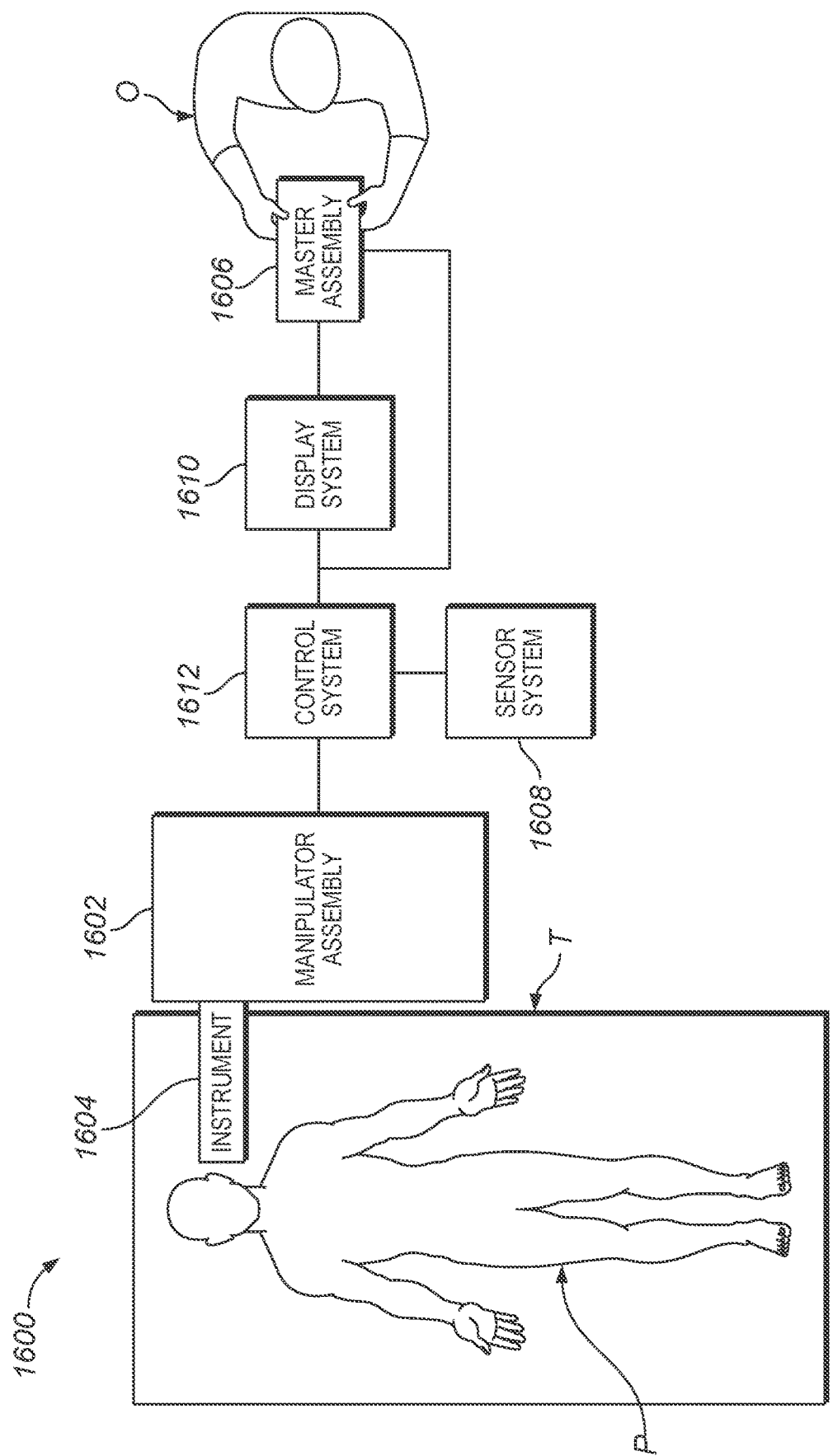
FIG. 16 is a schematic representation of a robotic or teleoperated medical system configured in accordance with various embodiments of the present technology.

FIG. 16 is a simplified diagram of a medical system ("system 1600") configured in accordance with embodiments of the present technology. In some examples medical system 1600 can be used to delivery instruments, such as apparatus 100/300/500/600/700/1000/1100/1200 and be used to perform methods 800, 900, and 1400. As shown in FIG. 16, the system 1600 generally includes a manipulator assembly 1602 to manipulate a medical instrument 1604 while performing various procedures on a patient P. The manipulator assembly 1602 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. The manipulator assembly 1602 can be mounted to an operating table T, or to a main support (e.g., a movable cart, stand, second table, etc.). The system may include a master control 1606 configured to allow an operator O (e.g., a surgeon, clinician, physician, etc.) to view the interventional site and to control the manipulator assembly 1602. The master assembly 1606 generally includes one or more input and control devices (not shown) for controlling the medical instrument 1604 via the manipulator assembly 1602 in a plurality of degrees of freedom. The input device may also include actuators for applying suction, vacuum, irrigation, and/or the like to the instrument 1604. The input and control devices of the master control 1606 may include a scroll wheel and a trackball. In an example implementation of the system 1600, the scroll wheel may be rolled forwards or backwards in order to control the advancement or retraction of the medical instrument 1604 with respect to the patient anatomy, and the trackball may be rolled in various directions by the operator O to steer the position of the distal end portion and/or distal tip of the medical instrument 1604, e.g., to control bend or articulation. Various systems and methods related to motion control consoles are described in PCT Pub. No. 2019/027922, filed Jul. 30, 2018, titled "Systems and Methods for Safe Operation of a Device", and U.S. Patent Pub. No. 2019/0029770, filed Jul. 30, 2018, titled "Systems and Methods for Steerable Elongate Device", which are incorporated by reference herein in their entireties.

The manipulator assembly 1602 may be configured to support and manipulate the medical instrument 1604 with a kinematic structure of one or more non-servo-controlled links (e.g., one or more links that may be manually positioned and locked in place, generally referred to as a set-up structure (SUS)), and/or one or more servo-controlled links (e.g., one or more powered links that may be controlled in response to commands). In some embodiments, the kinematic structure may be locked in place or unlocked to be manually manipulated by the operator O interacting with switches, buttons, or other types of input devices. Accordingly, the manipulator assembly 1602 may be configured to position the medical instrument 1604 at an optimal position and orientation relative to patient anatomy or other medical devices. In this regard, the manipulator assembly 1602 may include a plurality of actuators or motors that drive inputs on the medical instrument 1604 in response to commands from a control system 1612. The actuators may include drive systems that when coupled to the medical instrument 1604 may advance the medical instrument 1604 into a naturally or surgically created anatomic orifice in the patient P. The drive systems may be included in the manipulator assembly 1602 to move the distal end of the medical instrument 1604 according to any intended degree of freedom, which may include three degrees of linear motion (e.g., linear motion along the X, Y, and/or Z Cartesian axes) and three degrees of rotational motion (e.g., rotation about the X, Y, and Z Cartesian axes).

As shown in FIG. 16, the system 1600 may include a sensor system 1608 with one or more sub-systems for receiving information about the instruments coupled to the instrument manipulator (not shown). Actuator position sensors, such as resolvers, encoders, potentiometers, and other mechanisms, may provide sensor data to the sensor system 1608 describing the rotation and orientation of the motor shafts of the instrument manipulator (not shown). Such position sensor data may be used to determine motion of the objects manipulated by the actuators. Such sub-systems may include a position/location sensor system (e.g., an electromagnetic (EM) sensor system); a shape sensor system for determining the position, orientation, speed, velocity, pose, and/or shape of a distal end, and/or of one or more segments along a flexible body that may make up a portion of the medical instrument 1604; and/or a visualization system for capturing images from the distal portion of the medical instrument 1604, among other possible sensors.

The control system 1612 may include at least one memory and at least one computer processor (not shown) for effecting control between the medical instrument 1604, the master control 1606, the sensor system 1608, and the display system. The control system 1612 may also include programmed instructions, which may be stored on a non-transitory machine-readable medium, to implement some or all of the methods described in accordance with aspects of the present technology disclosed herein, including instructions for providing information to the display system. The control system 1612 may include two or more data processing circuits with one portion of the processing optionally being performed on or adjacent to the manipulator assembly 1602, another portion of the processing being performed at the master control 1606, etc. The processors of the control system 1612 may execute instructions for the processes disclosed herein. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, the control system 1612 supports wireless communication protocols, such as Bluetooth, IrDA, HomeRF, IEEE 802.16, DECT, Wireless Telemetry, and the like.

The system 1600 may further include optional operations and support systems (not shown) such as tracking systems, navigation systems, control systems, imaging systems, illumination systems, steering control systems, irrigation systems, and/or suction systems. In some embodiments, the foregoing systems can be coupled, components of foregoing systems or of other systems, or separate systems. For example, the tracking system can be coupled to the sensor system, the navigation system can be a component of the control system, the control system can include the navigation system, the imaging system can be a separate system, or a combination thereof. In some embodiments, the system 1600 may include more than one manipulator assembly and/or more than one master control. The exact number of teleoperational manipulator assemblies can be tailored for the surgical procedure to be performed and/or the space constraints within the operating room, among other factors. Multiple master controls may be collocated or positioned in separate locations. Multiple master controls allow more than one operator to control one or more teleoperational manipulator assemblies in various combinations.

Figures 17A, 17B:
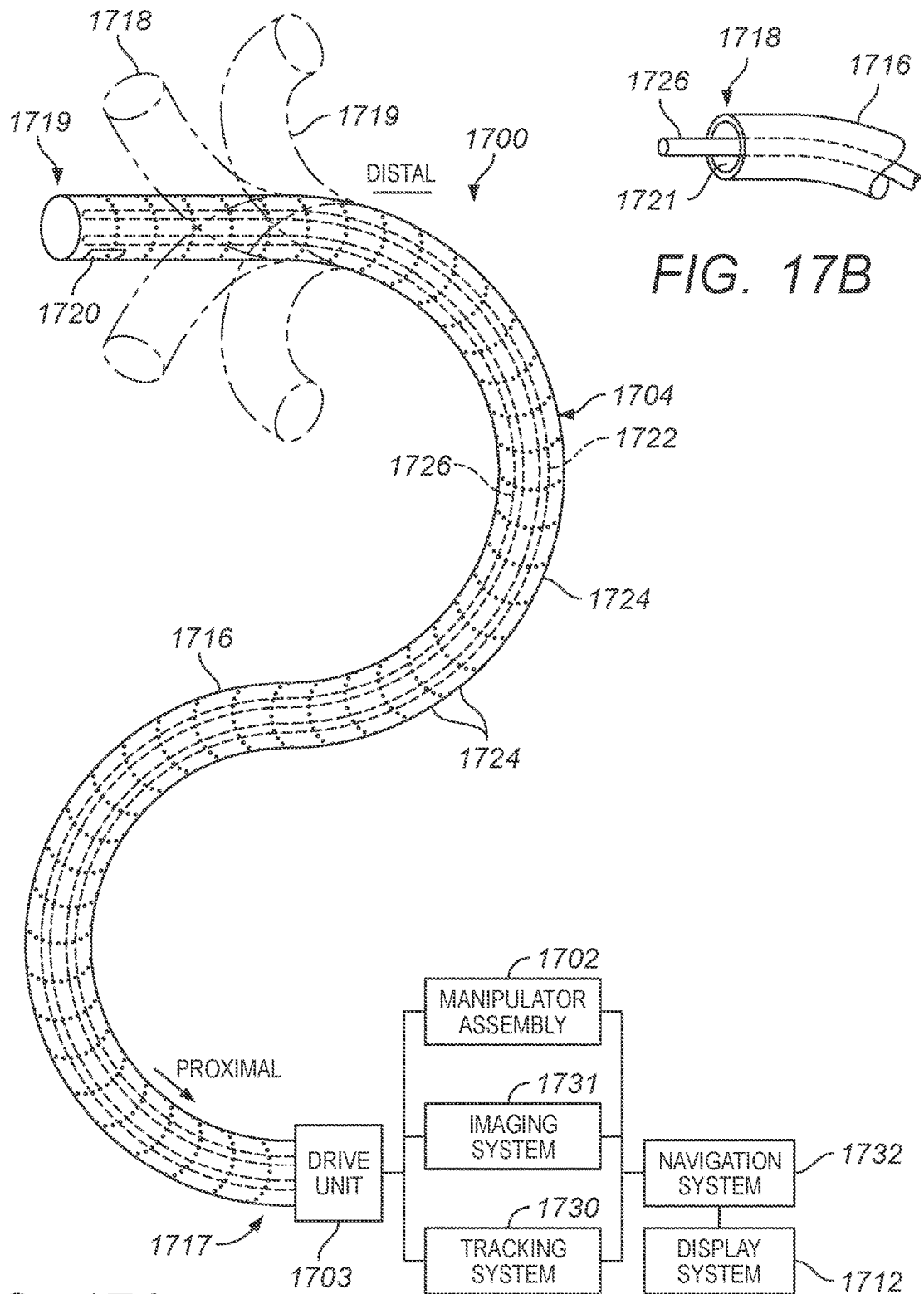
FIG. 17A is a simplified diagram of a medical instrument system configured in accordance with various embodiments of the present technology.
FIG. 17B is a simplified diagram of a medical instrument system configured in accordance with various embodiments of the present technology.

FIG. 17A is a simplified diagram of a medical instrument system 1700 according to some embodiments. Medical instrument system 1700 includes an instrument, such as elongate device 1704, coupled to a drive unit 1703 which can be integrated in or supported by manipulator assembly 1702. Medical instrument system 1700 further includes a tracking system 1730, an imaging system 1731, a navigation system 1732 and a display system 1712. Elongate device 1704, manipulator assembly 1702, and display system 1712 can be similar in structure and function as instrument 1604, manipulator 1602, and display system 1610 respectively. Additionally, drive unit 1703, manipulator assembly 1702, imaging system 1731, tracking system 1730, navigation system 1732, and display system 1712 may all couple to a control system (not shown) such as control system 1612 and a master control (not shown) such as master assembly 1606.

Elongate device 1704 includes a flexible body 1716 having proximal end 1717 and a distal end 1719 with a tip portion 1718. The flexible body 1716 may house cables, linkages, or other steering controls (not shown) that extend between the drive unit 1703 and distal end 1719 to controllably bend distal end 1719 as shown, for example, by broken dashed line depictions of distal end 1719. In some examples, at least four cables are used to provide independent "up-down" steering to control a pitch of distal end 1719 and "left-right" steering to control a yaw of distal end 1719. Various elongate devices are described in PCT Pub. No. WO 2019/018736, filed Jul. 20, 2018, titled "Flexible Elongate Device Systems and Methods," which is incorporated by reference herein in its entirety.

The flexible body 1716 additionally includes a channel 1721 sized and shaped to receive a medical instrument 1726. FIG. 17B, for example, is a simplified diagram of flexible body 1716 with medical instrument 1726 extended according to some embodiments. In some embodiments, medical instrument 1726 may be used for procedures such as imaging, visualization, surgery, biopsy, material removal, ablation, illumination, irrigation, or suction. Medical instrument 1726 can be deployed through channel 1721 of flexible body 1716 and used at a target location within the anatomy. Medical instrument 1726 may include, for example ureteroscopes, endoscopes, duodenoscopes, and/or the like including any of the flexible apparatuses described above such as flexible apparatuses 100, 300, 500, 600, 700, 1000, 1100, and 1200. Medical instrument 1726 may further include or deliver image capture probes, biopsy instruments, laser ablation or fragmentation fibers, baskets, meshes, and/or other surgical, diagnostic, or therapeutic tools. Medical instrument 1726 may be used with an imaging instrument (e.g., an image capture probe) also within flexible body 1716. The imaging instrument may include a cable coupled to the camera for transmitting the captured image data. In some examples, the imaging instrument may be a fiber-optic bundle, such as a fiberscope, that couples to image processing system 1731. The imaging instrument may be single or multi-spectral—for example, capturing image data in one or more of the visible, infrared, and/or ultraviolet spectrums. Medical instrument 1726 may be advanced from the opening of channel 1721 to perform the procedure and then retracted back into the channel when the procedure is complete. Medical instrument 1726 may be removed from proximal end 1717 of flexible body 1716 or from another optional instrument port (not shown) along flexible body 1716. Flexible devices receiving medical instruments are described in detail in U.S. Pat. No. 9,452,276, filed Oct. 14, 2011, disclosing "Access sheath with Removable Vision Probe", and which is incorporated by reference herein in its entirety.

In various embodiments, medical instrument 1726 (e.g., apparatuses 100, 300, 500, 600, 700, 1000, 1100, and 1200) may be coupled to drive unit 1703, manipulator assembly 1702 or a separate second drive unit (not shown) or second manipulator assembly (not shown) and be controllably or robotically bendable using steering controls. Additionally, the drive unit 1703 or manipulator assembly 1702 may include actuators that can be used to insert, rotate, articulate the medical instrument 1726 in bending (e.g. pitch or yaw), and/or actuate an articulable end effector (not shown) of the medical instrument 1726 for grasping tissue in the jaws of a biopsy device, opening and closing a basket, and/or the like.

Medical instrument system 1700 further includes tracking system 1730 for determining the position, orientation, speed, velocity, pose, and/or shape of distal end 1719 and/or of one or more segments 1724 along flexible body 1716. Tracking system 1730 may use data or information from a sensor system, such as sensor system 1608, including one or more sensors and/or imaging devices as described in further detail below. The sensor system may include a shape sensor 1722 for optionally tracking distal end 1719 and/or one or more of the segments 1724. Shape sensor 1722 may optionally include an optical fiber aligned with flexible body 1716 (e.g., provided within an interior channel (not shown) or mounted externally). The optical fiber of shape sensor 1722 forms a fiber optic bend sensor for determining the shape of flexible body 1716. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. Pat. No. 7,781,724, filed Sep. 26, 2006, disclosing "Fiber optic position and shape sensing device and method relating thereto"; U.S. Pat. No. 7,772,541, filed Mar. 17, 2008, disclosing "Fiber Optic Position and/or Shape Sensing Based on Rayleigh Scatter"; and U.S. Pat. No. 6,389,187, filed Apr. 21, 2000, disclosing "Optical Fiber Bend Sensor", which are all incorporated by reference herein in their entireties. In some embodiments, tracking system 1730 may optionally and/or additionally track distal end 1719 using a position sensor system 1720. Position sensor system 1720 may be a component of an EM sensor system with position sensor system 1720 including one or more conductive coils that may be subjected to an externally generated electromagnetic field. In some embodiments, position sensor system 1720 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

In some embodiments, an optical fiber sensor may be used to measure temperature, pressure, or force. In some embodiments, a temperature sensor, a force sensor, an impedance sensor, or other types of sensors may be included within the flexible body. In various embodiments, one or more position sensors (e.g. fiber shape sensors, EM sensors, and/or the like) may be integrated within the medical instrument 1726 and used to track the position, orientation, speed, velocity, pose, and/or shape of a distal end or portion of medical instrument 1726 using the tracking system 1730.

The information from tracking system 1730 may be sent to navigation system 1732 where it is combined with information from image processing system 1731 and/or the preoperatively obtained models to provide the operator with real-time position information. In some examples as will be described in further detail below, the control system may utilize the position information as feedback for positioning medical instrument system 1700. In some examples, the real-time position information may be displayed on display system 1712 of FIG. 17A for use in the control of medical instrument system 1700.

In one example, display system 1712 may be used for displaying images of the surgical site recorded pre-operatively or intra-operatively, and/or an image or representation of the surgical site and the elongate device 1704 and/or medical instrument 1726 using information from the sensor system 1608. The display system may use image data from the imaging system 1731 provided using imaging technology, such as by computed tomography (CT), magnetic resonance imaging (MRI), fluoroscopy, thermography, ultrasound, optical coherence tomography (OCT), thermal imaging, impedance imaging, laser imaging, nanotube X-ray imaging, endoscopic images and the like, or combinations thereof. The pre-operative or intra-operative image data may be presented as two-dimensional, three-dimensional, or four-dimensional (including e.g., time based or velocity-based information) images and/or as images from models created from the pre-operative or intra-operative image data sets. The display system 1712 and the master control (not shown) may be oriented such that the operator O can control the medical instrument 1704 and the master control with the perception of telepresence.

The display of visual indicators, markers, and/or images on the display system may be altered by input devices (e.g., buttons, switches, etc.) on the manipulator assembly 1702 and/or the master control. For example, actuating button or switch can cause a marker to be placed in a rendered model of patient anatomy displayed on the display system. The marker could correspond to an area within the patient at which a procedure (e.g., biopsy, treatment, stone fragmentation, stone removal) has been performed, or otherwise indicate an actual location within the patient anatomy where the medical instrument has been positioned. Such a virtual navigational marker may be dynamically referenced with registered preoperative or concurrent images or models. Systems and methods for registration are provided in PCT Pub. No. WO 2016/191298, published Dec. 1, 2016, titled "Systems and Methods of Registration for Image Guided Surgery", and in U.S. Pat. No. 8,900,131, filed May 13, 2016, titled "Medical System Providing Dynamic Registration of a Model of an Anatomic Structure for Image-Guided Surgery", which are incorporated by reference herein in their entireties.

The display system 1712 may further provide navigation assistance from the navigation system 1732, via the display system 1712 to the operator O when controlling the medical instrument 1704 during an image-guided surgical procedure. Virtual navigation may be based upon reference to an acquired preoperative or intraoperative dataset of anatomic passageways from the imaging system 1731. During a virtual navigation procedure, the sensor system may be used to compute an approximate location of the medical instrument 1704 with respect to the anatomy of the patient P. The location can be used to produce both macro-level tracking images (external to the anatomy of patient P) and virtual images (internal to the anatomy of patient P). The control system may implement one or more EM sensor, fiber optic sensors, and/or other sensors to register and display a medical implement together with preoperatively recorded surgical images, such as those from a virtual visualization system. For example, PCT Pub. No. WO 2016/191298 (published Dec. 1, 2016, titled "Systems and Methods of Registration for Image Guided Surgery"), which is incorporated by reference herein in its entirety, discloses one such system. Various systems and methods for monitoring the shape and relative position of an optical fiber in three dimensions are described in U.S. Pat. No. 7,781,724, filed Sep. 26, 2006, titled "Fiber Optic Position and Shape Sensing Device and Method Relating Thereto"; U.S. Pat. No. 7,772,541, filed on Mar. 12, 2008, titled "Fiber Optic Position and/or Shape Sensing Based on Rayleigh Scatter"; and U.S. Pat. No. 6,389,187, filed on Jun. 17, 1998, titled "Optical Fiber Bend Sensor," which are all incorporated by reference herein in their entireties.

The systems 1600 and 1700 may be suitable for use in surgical, diagnostic, therapeutic, or biopsy procedures, among others. While some embodiments of the system 1600/1700 are described herein with respect to such procedures, references to specific medical or surgical instruments and medical or surgical methods is not intended to limit the scope of the present technology. The systems, instruments, and methods described herein may be used for humans, animals, human cadavers, animal cadavers, portions of human or animal anatomy, and/or non-surgical diagnosis, as well as industrial systems and general robotic or teleoperational systems.

In one example, it can be helpful to provide methods and apparatus for delivery of apparatuses configured for, use in procedures that requires suction and/or irrigation and imaging, such as ureteroscopes for removing material at an anatomic location. The following will describe use of a robotic or teleoperated system such as system 1600/1700 for effectively navigating the apparatus from the anatomic opening (e.g. a natural or artificially created orifice), through potentially tortuous anatomy or through an organ, to the particular anatomic target location within the organ. In one embodiment, the apparatus may be delivered using a separate steerable sheath, for example instrument 1604 or elongate device 1704.

Figure 18A:
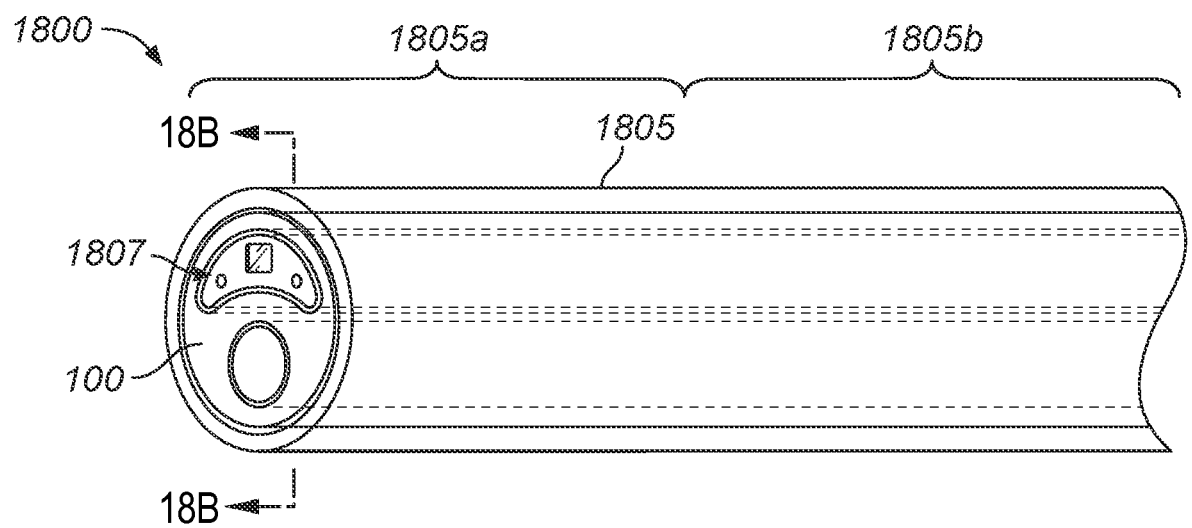
FIG. 18A illustrates a portion of an apparatus, such as a medical instrument, configured in accordance with embodiments of the present technology.
Figure 18B:
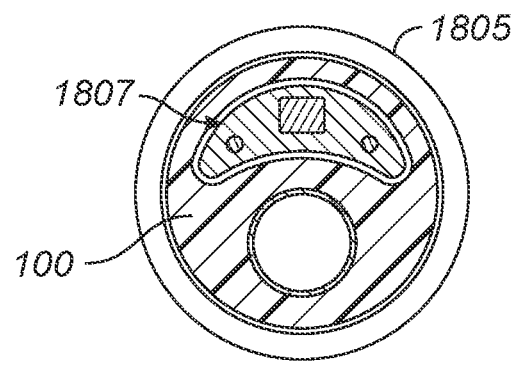
FIG. 18B is a cross-sectional view taken along line 18B-18B of FIG. 18A.

FIG. 18A illustrates an assembly 1800 configured in accordance with another embodiment of the present technology, and FIG. 18B is a cross-sectional view of the assembly 1800 taken along line 18B-18B of FIG. 18A. Referring to FIGS. 18A and 18B together, the assembly 1800 includes an elongated access sheath 1805 having a distal region 1805a and a proximal region 1805b. Elongated access sheath 1805 may be similar in structure and function as instrument 1604 or elongate device 1704 previously described. In these and other embodiments, a stiffness or rigidity of the access sheath 1805 of FIG. 18, the instrument 1604 of FIG. 16, and/or the elongate device 1704 of FIG. 17A can be uniform or can vary in a manner consistent with the discussion of the elongated shaft 110 of FIG. 1A above (e.g., by varying material compositions, material durometers, shaft or material dimensions, cut out dimensions, cut out spacings, etc.).

Apparatus 100 of FIGS. 18A and 18B is removably disposed within and carried by the elongated access sheath 1805. In some embodiments, the elongated access sheath 1805 is manually steerable, robotically steerable, and/or teleoperably steerable for delivery through patient anatomy to the target treatment site. In these embodiments, the apparatus 100 may be configured to be steerable independent of the steerable access sheath 1805. The apparatus 100 is configured to be distally advanced from and/or proximally retracted within the elongated access sheath 1805. In some configurations, for example, the apparatus 100 may be distally extended beyond the distal region 1805a of the elongated access sheath 1805 such that a portion of the apparatus 100 is distal to the distal region 1805a, a portion of the apparatus 100 remains disposed within the distal region 1805a, and a portion of the apparatus 100 remains disposed within the proximal region 1805b of the access sheath. The access sheath 1805 is an optional component that may not be used with the apparatus 100 in some embodiments of the present technology. In other embodiments, apparatuses of the present disclosure may be used with an access sheath, such as access sheath 1805 despite drawings not including an access sheath.

The access sheath 1805 can be configured to carry the apparatus for delivery though the patient's anatomy to the target site. In one embodiment, the access sheath 1805 is delivered and parked at a target location, e.g. a location near target material such as a target kidney stone. The access sheath 1805 may be delivered under external imaging (e.g. fluoroscopy or intra-operative CT) and/or an endoscopic camera may be provided within a lumen of the access sheath 1805 or may be integrated into a wall of the access sheath 1805. The access sheath 1805 can be positioned at a location and orientation so that a distal end of the access sheath 1805 is oriented towards the target stone. The parked access sheath 1805 provides a stable platform for a procedure. In this embodiment, the endoscopic camera can be removed from the access sheath 1805 and the apparatus 100 with imaging probe 170, can then be inserted through a proximal end of the access sheath 1805 to the distal end of the access sheath 1805. The apparatus 100 can then be further extended past the distal end of the access sheath 1805 and positioned to visually locate the target stone. The apparatus 100 can be positioned in close proximity to the target stone for retrieval, for example using method 800. If necessary, the access sheath 1805 may be repositioned for better access to the target stone based on the imaging data provided by the imaging probe 170.

In another embodiment, the apparatus 1800 (including imaging probe 1807) and the access sheath 1805 are delivered to the target location together. The imaging probe 1807 can provide endoscopic visualization of anatomy as the access sheath 1805 is being navigated through potentially tortuous anatomy and the target organ. Once positioned at the target location, the access sheath 1805 is parked providing a stable platform for target material retrieval, for example using methods such as method 800.

A portion of each or the entirety of each of the apparatuses, devices, instruments, systems, and methods described herein may be manually, robotically, and teleoperably controlled or performed. In some embodiments, one or more of the steerable apparatus, steerable instrument, and imaging probe are independently steerable. The steerable apparatus, steerable instrument, and imaging probe may each be configured to independently be manually steerable, robotically steerable, or teleoperably steerable.

In some examples, medical instrument system 1700 may be teleoperated within medical system 1600 of FIG. 16. In some embodiments, manipulator assembly 1606 of FIG. 16 may be replaced by direct operator control. In some examples, the direct operator control may include various handles and operator interfaces for hand-held operation of the instrument.

The apparatuses, instruments, devices, systems, and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described herein. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, a read only memory (ROM), a flash memory, an erasable programmable read only memory (EPROM), flash memory or other solid-state memory technology, CD-ROM, DVD, or other optical storage, magnetic disk storage, or any other hardware medium which can be used to store desired information and that can be accessed by components of the system. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

Medical tools that may be delivered through the flexible elongate devices or access sheaths disclosed herein may include, for example, image capture probes, biopsy instruments, laser ablation fibers, and/or other surgical, diagnostic, or therapeutic tools. Medical tools may include integrally formed and/or separately attached end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between its proximal and distal ends to controllably bend the distal end of an instrument. Steerable instruments are described in detail in U.S. Pat. No. 7,416,681, filed Oct. 4, 2005, disclosing "Articulated Surgical Instrument for Performing Minimally Invasive Surgery with Enhanced Dexterity and Sensitivity," and U.S. Pat. No. 9,259,274, filed Sep. 30, 2008, disclosing "Passive Preload and Capstan Drive for Surgical Instruments", and both of which are incorporated by reference herein in their entireties.

The apparatuses, instruments, devices, and systems described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like. In some embodiments, the apparatuses, instruments, devices, and systems described herein may be suited for removal of material from a subject, such as a kidney stone or tissue (e.g., a biopsy).

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near-complete lack of an action, characteristic, property, state, structure, item, or result.

The above detailed descriptions of embodiments of the technology are not intended to be exhaustive or to limit the technology to the precise form disclosed above. More specifically, while certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art. Various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other. Furthermore, the same shading may be used to indicate materials in cross section that can be compositionally similar, but the use of the same shading does not imply that the materials should be construed to be identical unless specifically noted herein.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A system for removal of material from a target location, the system comprising:
   an elongated shaft having a proximal portion, a distal portion, and a first elongated channel extending from the proximal portion to the distal portion;
   a tool extendable through the first elongated channel; and
   an imaging probe slidably disposed within a length of the first elongated channel, the imaging probe including a distal head assembly substantially centered on a proximal cable assembly, the distal head assembly configured to extend beyond a first channel opening defined in a distal surface of the distal portion to create a space between the first channel opening and a proximal surface of the distal head assembly to allow the tool to extend through the first channel opening and through the space,
   wherein a shape of the distal head assembly corresponds to a shape of the first channel opening, thereby preventing the tool from extending through the first channel opening before the space between the first channel opening and the proximal surface of the distal head assembly is created, and
   wherein the proximal cable assembly includes a rigidizable element configured to selectively maintain an alignment of the extended distal head assembly and the first channel opening.

2. The system of claim 1 wherein the proximal cable assembly has a first diameter, the distal head assembly has a second diameter, and wherein the first diameter is less than the second diameter.

3. The system of claim 1 wherein the tool is a basket, a laser, an ultrasound probe, a hydraulic fragmentation probe, a mechanical fragmentation probe, forceps, or a needle.

4. The system of claim 1, wherein the tool is usable through the first elongated channel after the tool has extended through the space.

5. The system of claim 1, wherein the elongated shaft further comprises a second elongated channel extending from the proximal portion to the distal portion.

6. The system of claim 5 wherein at least one of the first elongated channel or the second elongated channel is non-concentric.

7. The system of claim 5, further comprising a fluid circulation apparatus coupled to the second elongated channel to provide suction to the target location for removal of the material through the second elongated channel.

8. The system of claim 7 wherein the fluid circulation apparatus is further coupled to the first elongated channel to provide fluid utilizable through the first elongated channel.

9. The system of claim 8, wherein the fluid is utilized through the first elongated channel after the distal head assembly has extended beyond the distal portion of the first elongated channel.

10. The system of claim 9, wherein the fluid circulation apparatus is configured to stop providing suction to the target location after the imaging probe identifies that the material at the target location is too large to be removed through the second elongated channel.

11. The system of claim 9, wherein the fluid circulation apparatus is configured to reverse a flow of the fluid through the first elongated channel after the imaging probe identifies that the material at the target location is too large to be removed through the second elongated channel.

12. The system of claim 8, wherein the fluid and the tool are simultaneously utilized through the first elongated channel after the distal head assembly has extended beyond the first channel opening.

13. The system of claim 7, wherein the tool is an energy emitting device and where in the tool is utilized after the imaging probe identifies that the material at the target location is too large to be removed through the second elongated channel.

14. The system of claim 5, wherein a cross-section of the first elongated channel is arcuate, and wherein a cross-section of the second elongated channel is round.

15. The system of claim 14, wherein the round cross-section of the second elongated channel is nested with the arcuate cross-section of the first elongated channel.

16. The system of claim 1, wherein extend through the first elongated channel and through the space comprises extending into the space.

17. The system of claim 1, wherein extend through the first elongated channel and through the space further comprises extending out of the space.

* * * * *